United States Patent [19]

Kitajima et al.

[11] Patent Number: 5,674,811

[45] Date of Patent: Oct. 7, 1997

[54] CYANOKETONE DERIVATIVE AND HERBICIDE CONTAINING IT AS AN ACTIVE COMPONENT

[75] Inventors: Toshio Kitajima; Tadashi Kobutani; Shozo Kato; Masao Yamaguchi, all of Yamaguchi-ken; Masahiko Ishizaki, deceased, late of Shizuoka-ken, all of Japan, by Shigeyo Ishizaki, Masayo Ishizaki, Yoshihiko Ishizaki,Yumi Ishizaki, Legal Heirs

[73] Assignee: Tokuyama Corporation, Tokuyama, Japan

[21] Appl. No.: 319,044

[22] Filed: Oct. 6, 1994

[30] Foreign Application Priority Data

Oct. 8, 1993 [JP] Japan .................. 5-253165

[51] Int. Cl.$^6$ .................. C07C 255/17; C07C 255/27; A01N 37/34; A01N 43/08

[52] U.S. Cl. .................. 504/309; 558/389; 558/392; 558/396; 548/170; 548/182; 548/187; 548/213; 548/217; 548/221; 548/225; 548/228; 548/229; 548/243; 548/255; 548/306.4; 548/307.1; 548/312.4; 548/314.7; 548/316.4; 548/324.1; 548/365.7; 548/366.1; 548/370.1; 548/484; 548/517; 548/527; 548/541; 548/542; 548/543; 548/551; 549/28; 549/52; 549/62; 549/416; 549/420; 549/437; 549/449; 546/114; 546/115; 546/116; 546/153; 546/193; 546/194; 546/201; 546/207; 546/208; 546/210; 546/211; 546/226; 546/242; 546/290; 544/133; 544/152; 544/182; 544/215; 544/283; 544/284; 544/298; 544/333; 544/353; 544/354; 544/367; 504/224; 504/225; 504/227; 504/229; 504/230; 504/235; 504/239; 504/240; 504/244; 504/246; 504/247; 504/248; 504/249; 504/251; 504/252; 504/257; 504/261; 504/266; 504/267; 504/269; 504/270; 504/271; 504/276; 504/275; 504/277; 504/279; 504/280; 504/282; 504/283; 504/284; 504/288; 504/289; 504/292; 504/294; 504/298; 504/312

[58] Field of Search .................. 558/389, 392, 558/396; 546/226, 114, 115, 116, 153, 193, 194, 201, 207, 208, 210, 211, 242, 290; 504/249, 312, 309, 269, 270, 271, 276, 275, 277, 279, 280, 282, 283, 284, 288, 289, 292, 294, 298, 224, 225, 227, 229, 230, 235, 239, 240, 244, 246, 247, 248, 251, 252, 257, 261, 266, 267; 548/170, 182, 187, 213, 217, 225, 228, 229, 243, 255, 306.4, 307.1, 312.4, 314.7, 316.4, 324.1, 365.7, 366.1, 370.1, 484, 517, 527, 541, 542, 543, 551; 549/28, 52, 62, 416, 420, 437, 449; 544/133, 152, 182, 215, 283, 284, 298, 333, 353, 354, 367

[56] References Cited

U.S. PATENT DOCUMENTS 5,234,894 8/1993 Ishizaki et al. .................. 504/224

FOREIGN PATENT DOCUMENTS 0281103 9/1988 European Pat. Off. .
0506373 9/1992 European Pat. Off. .

OTHER PUBLICATIONS

English Language Abstract of JP-60-11451, (8)1985.
English Language Abstract of JP-57014503, Jan. 25, 1982.

*Primary Examiner*—Johann Richter
*Assistant Examiner*—Laura L. Stockton
*Attorney, Agent, or Firm*—Sherman and Shalloway

[57] ABSTRACT

A cyanoketone derivatives of the following formula (1)

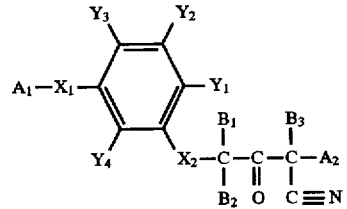

which are characterized by excellent herbicidal activity and effectiveness against a variety of broad leafed weeds, including barnyard grass, green foxtail, velvet leaf, livid amaranth and hairy beggar ticks.

28 Claims, No Drawings

CYANOKETONE DERIVATIVE AND HERBICIDE CONTAINING IT AS AN ACTIVE COMPONENT

DETAILED DESCRIPTION OF THE INVENTION

The present invention relates to a novel cyanoketone derivative and a herbicide containing it as an active component.

A variety of compounds have been tested on their herbicidal activities, and many herbicidal compounds are commercially available.

For example, Japanese Laid-open Patent Application (Kokai) No. 14,503/1982 discloses a nitrodiphenyl ether compound of the following formula (2)

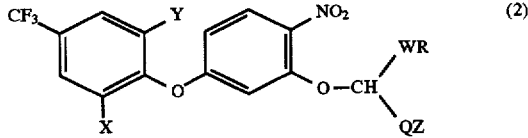

wherein X is halogen, hydrogen, a trifluoromethyl group, a $C_1$–$C_4$ alkyl group, a cyano group or a nitro group, Y is halogen, hydrogen or a trifluoromethyl group, W is oxygen or $S(O)_p$ in which p is 0 to 2, R is a $C_1$–$C_4$ alkyl group, a phenyl group, a halogen-substituted phenyl group, a trifluoromethyl-substituted phenyl group or a mononuclear aralkyl group having up to 12 carbon atoms, Q is $(CH_2)_n$ in which n is 0 to 4 or a $C_2$–$C_6$ alkenylene group, and Z is —$CO_2R^1$, —$C_2H$, —$CO_2$, —$CONH_2$, —$CONHR^1$, —$COSR^1$, —$CON(R^1)_2$, —CN, —$CH_2OH$, —$CH_2Cl$, —$COR^1$, —$OR^1CH_2OCH_3$ or —$CO(CR^2R^3)_mCO_2R^1$ in which $R^1$ is a $C_1$–$C_4$ alkyl group, a $C_3$–$C_6$ alkenyl group, a $C_1$–$C_4$ cyanoalkyl group, a $C_3$–$C_6$ alkynyl group, a $C_2$–$C_4$ haloalkyl group, a $C_1$–$C_4$ alkoxyalkyl group, a trifluoromethyl group, a $C_2$–$C_4$ nitroalkyl group or a mononuclear aralkyl group having up to 12 carbon atoms, each of $R^2$ and $R^3$ is independently hydrogen or a methyl group, and m is an integer of 1 to 3, and that said nitrodiphenyl ether compound has a herbicidal activity on weeds such as barnyardgrass, *Bromus pauciflorus*, nutgrass, broad cocklebur and African marigold.

On the other hand, Japanese Laid-open Patent Application No. 11452/1985 discloses α-cyanoketones of the following formula (3)

which are a compound of the above formula (3) in which $R_1$ is an alkyl group or an aromatic group and $R_2$ is an alkyl group having at least 3 carbon atoms, an aralkyl group, an aromatic group or a heterocyclic group and a compound of the formula (6) in which $R_1$ is a heterocyclic group, a substituted phenoxy or substituted thiophenoxy group and $R_2$ is a hydrogen atom, an alkyl group, an aromatic group or a heterocyclic group, and that such α-cyanoketones has a herbicidal activity on a variety of weeds such as southern crabgrass, barnyardgrass, tufted knotweed and slender amaranth when these are applied in a high dosage (foliar application test).

Some of the present inventors have found a cyanoketone derivative and herbicide containing it as an active component represented by the following formula (4) and have already proposed this finding (see U.S. Pat. No. 5,234,894).

The cyanoketone derivative of the following formula (4) has remarkably high herbicidal activity and is effective against a variety of gramineous weeds. Examples of the weeds against which the herbicidal activity is generally effective include upland soil gramineous weeds such as fall panicum, green foxtail, sorghum, wild oat, Japanese brome, water foxtail, annual bluegrass, barnyardgrass, Johnsongrass, quackgrass, southern crabgrass, goosegrass, Italian ryegrass, burmudagrass and knotgrass.

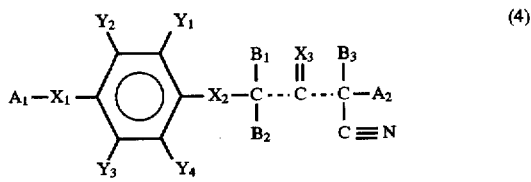

wherein $A_1$ is a substituted or unsubstituted phenyl or naphthyl group, or a substituted or unsubstituted heterocyclic group selected from the group consisting of a 5-membered ring, a 6-membered ring, a 5- and 6-membered fused ring group and a 6- and 6-membered fused ring group, substituents of said substituted phenyl, naphthyl and heterocyclic groups being selected from the group consisting of a halogen atom, an alkyl group having 1 to 4 carbon atoms, a halogenoalkyl group having 1 to 4 carbon atoms, an alkoxy group having 1 to 4 carbon atoms, an alkylthio group having 1 to 4 carbon atoms, and alkoxycarbonyl group having 1 to 6 carbon atoms, a nitro group and a cyano group;

each of $X_1$, $X_2$ and $X_3$ is independently an oxygen or sulfur atom; each of $B_1$, $B_2$ and $B_3$ is independently a hydrogen atom or alkyl group having 1 to 6 carbon atoms; each of $Y_1$, $Y_2$, $Y_3$ and $Y_4$ is independently a hydrogen atom, a halogen atom or alkyl group having 1 to 6 carbon atoms; and $A_2$ is substituted or unsubstituted group selected from the group consisting of an alkyl group having 1 to 6 carbon atoms, an alkenyl group having 2 to 6 carbon atoms, an alkynyl group having 2 to 6 carbon atoms, an alkoxy group having 1 to 4 carbon atoms, an alkylthio group having 1 to 4 carbon atoms and an alkoxycarbonyl group having 1 to 6 carbon atoms, substituents of said substituted groups being selected from the group consisting of a halogen atom, an alkoxy group having 1 to 4 carbon atoms, an alkylthio group having 1 to 4 carbon atoms, a tetrahydrofuryl group and a cyano group; and unsubstituted benzoyl group; a halogen substituted benzoyl group; a cyano group of the group as defined in $A_1$;

provided that when $B_1$ is a hydrogen atom and $B_2$ is alkyl, the compound of the formula (4) is an R- or S-enantiomers with regard to the asymmetric carbon to which $B_1$ and $B_2$ are bonded or a mixture of these enantiomers.

It is an object of the present invention to provide a novel cyanoketone derivative.

It is another object of the present invention to provide a herbicide containing the cyanoketone derivative of the present invention as a herbicidal active component.

It is further another object of the present invention to provide a novel cyanoketone derivative which exhibits high selectivity and high herbicidal activity and a herbicide containing this derivative.

It is still further another object of the present invention to provide a herbicide which has high herbicidal activity on broad-leaved weeds even when used in a low dosage and which is much safe even when applied to intended crop in a high dosage.

Other objects and advantages of the present invention will be apparent from the following description.

According to the present invention, the above objects and advantages of the present invention are achieved, first, by a cyanoketone derivative of the following formula (1)

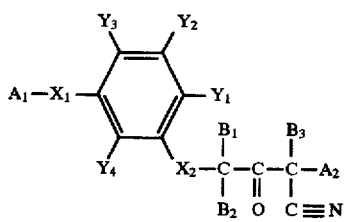

wherein $A_1$ is a substituted or unsubstituted phenyl or naphthyl group, or a substituted or unsubstituted heterocyclic group selected from the group consisting of a 5-membered ring, a 6-membered ring, a 5- and 6-membered fused ring group and a 6- and 6-membered fused ring group, substituents of said substituted phenyl, naphthyl and heterocyclic groups being selected from the group consisting of a halogen atom, an alkyl group having 1 to 4 carbon atoms, a halogenoalkyl group having 1 to 4 carbon atoms, an alkoxy group having 1 to 4 carbon atoms, an alkylthio group having 1 to 4 carbon atoms, and an alkoxycarbonyl group having 1 to 6 carbon atoms in alkyl moiety, a nitro group and a cyano group;

each of $X_1$ and $X_2$ is independently an oxygen or sulfur atom; each of $B_1$, $B_2$ and $B_3$ is independently a hydrogen atom or alkyl group having 1 to 6 carbon atoms;

$Y_1$ is a hydrogen atom, a nitro group or a halogen atom;

each of $Y_2$, $Y_3$ and $Y_4$ is independently a hydrogen atom, a halogen atom or an alkyl group having 1 to 6 carbon atoms;

$A_2$ is a substituted or unsubstituted alkyl group having 1 to 6 carbon atoms, an alkenyl group having 2 to 6 carbon atoms, an alkynyl group having 2 to 6 carbon atoms, an alkoxy group having 1 to 4 carbon atoms, an alkylthio group having 1 to 4 carbon atoms, alkoxycarbonyl group having 1 to 6 carbon atoms in alkyl moiety, a cyano group, a substituted or unsubstituted benzoyl group, a group as defined in $A_1$ or a group of

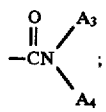

substituents of said substituted alkyl group and said substituted benzoyl group are selected from the group consisting of a halogen atom, an alkoxy group having 1 to 4 carbon atoms, an alkylthio group having 1 to 4 carbon atoms, a cyano group and a tetrahydrofuryl group;

each of $A_3$ and $A_4$ is independently selected from the group consisting of a hydrogen atom, a substituted or unsubstituted alkyl group having 1 to 6 carbon atoms, an alkenyl group having 2 to 6 carbon atoms, an alkynyl group having 2 to 6 carbon atoms, an alkoxy group having 1 to 4 carbon atoms, an alkylthio group having 1 to 4 carbon atoms, an alkoxycarbonyl group having 1 to 6 carbon atoms in alkyl moiety and a group as defined in $A_1$;

and both $A_3$ and $A_4$ can form saturated or unsaturated ring which may contain a hetero atom;

provided that when one of $B_1$ or $B_2$ is a hydrogen atom and the other is alkyl, the compound of the formula (1) is an R- or S-enantiomers with regard to the asymmetric carbon to which $B_1$ and $B_2$ are bonded or a mixture of these enantiomers.

The cyanoketone derivative represented by the formula (1) of the present invention has a strong selective herbicidal activity compared to the cyanoketone derivative of the formula (4) which is described in said U.S. Pat. No. 5,234,894, and therefore exhibits a herbicidal activity to a variety of broad-leaved weeds in a smaller amount.

In the above formula (1), $A_1$ is a substituted or unsubstituted aromatic group, or a substituted or unsubstituted heterocyclic group.

The aromatic group preferably includes phenyl and naphthyl.

The heterocyclic group preferably includes five-membered or six-membered cyclic groups having at least one hereto atom selected from the group consisting of oxygen, sulfur and nitrogen atoms.

Examples of such heterocyclic groups preferably include 5-membered cyclic groups such as furyl, thienyl, pyrrolyl, imidazolyl, pyrazolyl, oxazolyl, thiazolyl, isoxazolyl and isothiazolyl groups; 6-membered ring groups such as pyridyl, pyranyl, thiopyranyl, piperazinyl, pyrimidinyl, triazinyl and cyclohexenyl groups; 5- and 6-membered fused ring groups such as benzofuranyl, benzothienyl, indolyl, benzoimidazolyl, benzothiazolyl, benzoxazolyl, oxazolopyridinyl and thiazolopyridinyl groups; and 6- and 6-membered fused ring groups-such as quinolyl, quinoxalinyl and quinazolinyl groups.

The substituent which may be substituted on these aromatic and heterocyclic groups includes a halogen atom such as chlorine, bromine, iodine and fluorine; an alkyl group having 1 to 4 carbon atoms such as methyl, ethyl, propyl and butyl; a halogenoalkyl group having 1 to 4 carbon atoms such as chloromethyl, difluoromethyl, trifluoromethyl, trifluoroethyl, perfluoroethyl, pentachloropropyl and perfluorobutyl; an alkoxy group having 1 to 4 carbon atoms such as methoxy, ethoxy, propoxy and butoxy; an alkylthio group having 1 to 4 carbon atoms such as methylthio, ethylthio, propylthio and butylthio; an alkoxycarbonyl group having 1 to 6 carbon atoms in alkyl moiety, such as methoxycarbonyl, ethoxycarbonyl, propoxycarbonyl and butoxycarbonyl; a nitro group; and a cyano group. These substituents are preferred particularly in an industrial point of view.

With respect to $A_1$, the substituted or unsubstituted phenyl group gives a higher herbicidal activity than the other groups. A compound in which a phenyl group is substituted with a halogen atom and/or a halogenoalkyl group shows an especially high herbicidal activity.

In the formula (1), each of $X_1$ and $X_2$ is, independently of the other, an oxygen or sulfur atom. In particular, an oxygen atom is preferred.

In the formula (1), each of $B_1$, $B_2$ and $B_3$ is, independently of the others, a hydrogen atom or alkyl. The alkyl preferably include a linear or branched alkyl group having 1 to 6 carbon atoms such as methyl, ethyl, propyl, butyl, heptyl and hexyl.

With respect to $B_1$ and $B_2$, a compound in which one of $B_1$ and $B_2$ is a hydrogen atom and the other is an alkyl group is especially preferable. It is preferred that $B_3$ is a hydrogen atom.

In the formula (1), $Y_1$ is a hydrogen atom, a nitro group or a halogen atom and in particular a nitro group or a halogen atom is preferred.

In the formula (1), each of $Y_2$, $Y_3$ and $Y_4$ is, independently of the others, a hydrogen atom, a halogen atom or alkyl group and in particular a hydrogen atom is preferred.

In $Y_1$, $Y_2$, $Y_3$ or $Y_4$, the halogen atom includes chlorine, bromine, iodine and fluorine. The alkyl may be linear or branched, and is preferably selected from an alkyl group having 1 to 6 carbon atoms such as methyl, ethyl, propyl, butyl, heptyl and hexyl.

In the formula (1), $A_2$ is a substituted or unsubstituted alkyl group having 1 to 6 carbon atoms, an alkenyl group having 2 to 6 carbon atoms, an alkynyl group having 2 to 6 carbon atoms, an alkoxy group having 1 to 4 carbon atoms, an alkylthio group having 1 to 4 carbon atoms, an alkoxycarbonyl group having 1 to 6 carbon atoms in alkyl moiety, a cyano group, a substituted or unsubstituted benzoyl group, a group as defined in $A_1$, or a group of

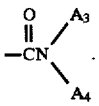

The alkyl group includes those specified concerning $Y_2$.

The substituent which may be substituted on the alkyl preferably includes a halogen atom, an alkoxy group having 1 to 4 carbon atoms, an alkylthio group having 1 to 4 carbon atoms, a tetrahydrofuryl group and a cyano group.

The alkyl group preferably includes methyl, ethyl, propyl, butyl, heptyl and buthoxy.

The alkenyl group preferably includes ethenyl, propenyl, butenyl, pentenyl and hexenyl.

The alkynyl group preferably includes ethynyl, propenyl, butynyl and hexynyl.

The alkoxy group preferably includes methoxy, ethoxy, propoxy and buthoxy.

The alkylthio group preferably includes methylthio, ethylthio, propylthio and butylthio.

The alkoxycarbonyl group preferably includes methoxycarbonyl, ethoxycarbonyl, propoxycarbonyl and butoxycarbonyl.

The substituent which may be substituted on benzoyl group preferably includes a halogen atom, an alkoxy group having 1 to 4 carbon atoms, an alkylthio group having 1 to 4 carbon atoms, a tetrahydrofuryl group and a cyano group.

Furthermore, $A_2$ can be a substituted or unsubstituted phenyl or naphthyl group, or a substituted or unsubstituted heterocyclic group as defined in $A_1$ or a group of

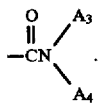

in the group of

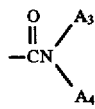

each of $A_3$ and $A_4$ is independently selected from the group consisting of a hydrogen atom, a substituted or unsubstituted alkyl group having 1 to 6 carbon atoms, an alkenyl group having 2 to 6 carbon atoms, an alkynyl group having 2 to 6 carbon atoms, an alkoxy group having 1 to 4 carbon atoms, an alkylthio group having 1 to 4 carbon atoms and an alkoxycarbonyl group having 1 to 6 carbon atoms in alkyl moiety, and a group as defined in $A_1$; and both $A_3$ and $A_4$ can form saturated or unsaturated ring which may contain a hetero atom.

The alkyl group includes those specified concerning $Y_2$.

The substituent which may be substituted on the alkyl preferably includes a halogen atom, an alkoxy group having 1 to 4 carbon atoms, an alkylthio group having 1 to 4 carbon atoms, a tetrahydrofuryl group and a cyano group.

The alkyl group preferably includes methyl, ethyl, propyl, butyl, heptyl and buthoxy.

The alkenyl group preferably includes ethenyl, propenyl, butenyl, pentenyl and hexenyl.

The alkynyl group preferably includes ethynyl, propynyl, butynyl, pentynyl and hexynyl.

The alkoxy group preferably includes methoxy, ethoxy, propoxy and buthoxy.

The alkylthio group preferably includes methylthio, ethylthio, propylthio and butylthio.

The alkoxycarbonyl group preferably includes methoxycarbonyl, ethoxycarbonyl, propoxycarbonyl and butoxycarbonyl.

When $A_3$ and $A_4$ together form a saturated or unsaturated ring which may contain a hetero atom, a nitrogen atom or an oxygen atom is used as the hetero atom and further an alkyl chain or an alkynyl chain required for forming a ring having 2 to 8 carbon atoms is preferably used. Specific examples of a cyclic group formed by $A_3$ and $A_4$ with the nitrogen atom bonded to $A_3$ and $A_4$ include ethyleneimino, pyrrolidyl, pyrrolyl, pyrrolinyl, pyrazyl, pyrazolinyl, imidazolyl, triazolyl, piperidino, morpholino, piperazinyl, indolyl and plynyl groups.

Among the above-described definitions of $A_3$ and $A_4$, the compound in which $A_3$ and $A_4$ together form the above ring is preferred because of its high herbicidal activity.

It Is preferred that $A_2$ of the formula (1) is a substituted or unsubstituted phenyl group or a group

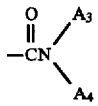

in which $A_3$ and $A_4$ together form a saturated or unsaturated ring which may contain a hetero atom.

Further, in the compound of the present invention, when one of $B_1$ and $B_2$ is a hydrogen atom and the other is an alkyl group, the compound of the formula (1) is an R- or S-enantiomer with regard to the asymmetric carbon to which $B_1$ and $B_2$ are bonded or a mixture of these enantiomers.

The compound of the above formula (1) preferably include the following compounds.

(100) 4-[5-(2-chloro-4-trifluoromethylphenoxy)-2-nitrophenoxy]-3-oxo-2-(2-pyridyl)pentanenitrile (102) 4-[5-(2-chloro-4-trifluoromethylphenoxy)-2-nitrophenoxy]-3-oxo-2-(2,4-dichlorophenyl)-2-pentanenitrile (104) 4-[5-(2-chloro-4-trifluoromethylphenoxy)-nitrophenoxy]-3-oxo-2-(3,4-dichlorophenyl)pentanenitrile (106) 4-[5-(2-chloro-4-trifluoromethylphenoxy)-2-nitrophenoxy]-3-oxo-2-(2,6-dichlorophenyl)pentanenitrile (108) 4-[5-(2-chloro-4-trifluoromethylphenoxy)-2-nitrophenoxy]-3-oxo-2-(3-chlorophenyl)pentanenitrile (110) 4-[5-(2-chloro-4-trifluoromethylphenoxy)-2-nitrophenoxy]-3-oxo-2-(3-bromophenyl)pentanenitrile (112) 4-[5-(2-chloro-4-trifluoromethylphenoxy)-2(3-nitrophenoxy]-3-oxo-2-phenylpentanenitrile (114) 4-[5-(2-chloro-4-trifluoromethylphenoxy)-2-nitrophenoxy]-3-oxo-2-(3-methylphenyl)pentanenitrile
(116) 4-[5-(2-chloro-4-trifluoromethylphenoxy)-2-nitrophenoxy]-3-oxo-2-(4,6-dichloro-2-pyrimidyl)pentanenitrile
(118) 4-[5-(2-chloro-4-trifluoromethylphenoxy)-2-nitrophenoxy]-3-oxo-2-(3-methoxymethylphenyl)pentanenitrile
(120) 4-[5-(2,4-dichlorophenoxy)-2-nitrophenoxy]-3-oxo-2-methylpentanenitrile
(122) 4-[5-(2-fluoro-4-chlorophenoxy)-2-nitrophenoxy]-3-oxo-2-cyanopentanenitrile
(124) 4-[5-(6-trifluoromethyl-2-naphtoxy)-2-nitrophenoxy]-3-oxo-2-(2,4-dichlorophenyl)pentanenitrile
(126) 4-[5-(7-chloro-2-naphtoxy)-2-nitrophenoxy]-3-oxo-2-(3-chlorophenyl)pentanenitrile (128) 4-[5-(7-methoxy-2-naphtoxy)-2-nitrophenoxy]-3-oxo-2-(5-methyl-2-thienyl)pentanenitrile
(130) 4-[5-(6-chloro-2-quinoxalinyloxy)-2-nitrophenoxy]-3-oxo-2-(1-tetrahydrofurfuryl)pentanenitrile
(132) 4-[5-(6-chloro-2-quinoxalinyloxy)-2-nitrophenoxy]-3-oxo-2-(3-trifluoromethylphenyl)pentanenitrile
(134) 4-[5-(6-chloro-2-quinoxalinyloxy)-2-nitrophenoxy]-3-oxo-2-(2,4-dichlorophenyl)pentanenitrile
(136) 4-[5-(2-chloro-4-trifluoromethylphenoxy)-2-nitrophenoxy]-3-oxo-2-(2,4-diclorophenyl)butyronitrile
(138) 4-[5-(2-chloro-4-trifluoromethylphenoxy)-2-nitrophenoxy]-3-oxo-2-(2,4-diclorophenyl)-2-methylpentanenitrile
(140) 4-[5-(2-chloro-4-methylphenoxy)-2-nitrophenoxy]-3-oxo-2-benzoylpentanenitrile
(142) 4-[5-(2-chloro-4-nitrophenoxy)-2-nitrophenoxy]-3-oxo-2-(3,4-dichlorophenyl)pentanenitrile
(144) 4-[5-(4-trifluoromethylphenylthio)-2-nitrophenoxy]-4-methyl-3-oxo-2-(2-propinyl)pentanenitrile
(146) 4-[5-(4-trifluoromethylphenylthio)-2-nitrophenylthio]-4-methyl-3-oxo-2-cyano-2-methylpentanenitrile
(148) 4-[5-(3-chloro-5-trifluoromethyl-2-pyridyloxy)-2-nitrophenylthio]-3-oxo-2-(2,4-dichlorophenyl)pentanenitrile
(150) 4-[5-(5-trifluoromethyl-2-pyridyloxy)-2-nitrophenoxy]-3-oxo-2-(2-chloro-4-methylphenyl)pentanenitrile
(152) 4-[5-(3-chloro-5-fluoro-2-pyridyloxy)-2-nitrophenylthio]-3-oxo-2-methylthiomethylbutyronitrile
(154) 4-[5-(5-fluoro-3-methyl-2-pyridyloxy)-2-nitrophenylthio]-4-methyl-3-oxo-2-trifluoromethylbutyronitrile
(156) 4-[5-(3-chloro-5-trifluoromethyl-2-pyridyloxy)-2-nitrophenoxy]-4-methyl-3-oxo-2-(2,4-dichlorophenyl)pentanenitrile
(158) 4-[5-(3-chloro-5-trifluoromethyl-2-pyridyloxy)-2-nitrophenoxy]-4-methyl-3-oxo-2-(2,4-dichlorophenyl)-2-methylpentanenitrile
(160) 4-[5-(2-chloro-4-trifluoromethylphenoxy)-2-nitrophenoxy]-3-oxo-2-(pyrrolidinylcarbonyl)pentanenitrile
(162) 4-[5-(2-chloro-4-trifluoromethylphenoxy)-2-nitrophenoxy]-3-oxo-2-(piperidinocarbonyl)pentanenitrile
(164) 4-[5-(2-chloro-4-trifluoromethylphenoxy)-2-nitrophenoxy]-3-oxo-2-[(1-cycloheptylamino)carbonyl]pentanenitrile
(166) 4-[5-(2-chloro-4-trifluoromethylphenoxy)-2-nitrophenoxy]-3-oxo-2-(morpholinocarbonyl)pentanenitrile
(168) 4-[5-(2-chloro-4-trifluoromethylphenoxy)-2-nitrophenoxy]-3-oxo-2-(4-methylpiperidinocarbonyl)pentanenitrile
(170) 4-[5-(2-chloro-4-trifluoromethylphenoxy)-2-nitrophenoxy]-3-oxo-2-(N-methoxycarbonyl-N-methylaminocarbonyl)pentanenitrile
(172) 4-[5-(2-chloro-4-trifluoromethylphenoxy)-2-nitrophenoxy]-3-oxo-2-(N,N-dimethylaminocarbonyl)pentanenitrile
(174) 4-[5-(2-chloro-4-trifluoromethylphenoxy)-2-nitrophenoxy]-3-oxo-2-(N-methyl-N-phenylaminocarbonyl)pentanenitrile
(176) 4-[5-(2-chloro-4-trifluoromethylphenoxy)-2-nitrophenoxy]-3-oxo-2-(N-ethyl-N-phenylaminocarbonyl)pentanenitrile
(178) 4-[5-(2-chloro-4-trifluoromethylphenoxy)-2-nitrophenoxy]-3-oxo-2-(N-isopropyl-N-phenylaminocarbonyl)pentanenitrile
(180) 4-[5-(2-chloro-4-trifluoromethylphenoxy)-2-nitrophenoxy]-3-oxo-2-(3,5-dimethylpiperidinocarbonyl)pentanenitrile
(182) 4-[5-(2-chloro-4-trifluoromethylphenoxy)-2-nitrophenoxy]-3-oxo-2-[N-methyl-N-(2,4-dichlorophenyl)aminocarbonyl]pentanenitrile
(184) 4-[5-(6-chloro-2-quinoxalinyloxy)-2-nitrophenoxy]-3-oxo-2-(N-ethoxymethyl-N-methylaminocarbonyl)pentanenitrile
(186) 4-[5-(6-trifluoromethyl-2-naphthoxy)-2-nitrophenoxy]-3-oxo-2-(N-methoxyethyl-N-methylaminocarbonyl)pentanenitrile
(188) 4-[5-(3-chloro-5-trifluoromethyl-2-pyridyloxy)-2-nitrophenoxy]-3-oxo-2-(N-methylaminocarbonyl)pentanenitrile
(190) 4-[5-(6-chloro-2-quinoxalinyloxy)-2-nitrophenoxy]-3-oxo-2-(piperidinocarbonyl)pentanenitrile
(192) 4-[5-(6-chloro-2-quinoxalinyloxy)-2-nitrophenoxy]-3-oxo-2-(N-ethyl-N-methoxyaminocarbonyl)pentanenitrile
(194) 4-[5-(2-benzothiazolyl)-2-nitrophenoxy]-3-oxo-2-(piperidinocarbonyl)pentanenitrile
(196) 4-[5-(2-chloro-4-trifluoromethylphenoxy)-2-chlorophenoxy]-3-oxo-2-(2-pyridyl)pentanenitrile
(198) 4-[5-(2-chloro-4-trifluoromethylphenoxy)-2-chlorophenoxy]-3-oxo-2-(2,4-dichlorophenyl)pentanenitrile
(200) 4-[5-(2-chloro-4-trifluoromethylphenoxy)-2-chlorophenoxy]-3-oxo-2-(3,4-dichlorophenyl)pentanenitrile
(202) 4-[5-(2-chloro-4-trifluoromethylphenoxy)-2-chlorophenoxy]-3-oxo-2-(2,6-dichlorophenyl)pentanenitrile
(204) 4-[5-(2-chloro-4-trifluoromethylphenoxy)-2-chlorophenoxy]-3-oxo-2-(3-chlorophenyl)pentanenitrile
(206) 4-[5-(2-chloro-4-trifluoromethylphenoxy)-2-chlorophenoxy]-3-oxo-2-(3-bromophenyl)pentanenitrile
(208) 4-[5-(2-chloro-4-trifluoromethylphenoxy)-2-chlorophenoxy]-3-oxo-2-phenylpentanenitrile
(210) 4-[5-(2-chloro-4-trifluoromethylphenoxy)-2-chlorophenoxy]-3-oxo-2-(3-methylphenyl)pentanenitrile
(212) 4-[5-(2-chloro-4-trifluoromethylphenoxy)-2-chlorophenoxy]-3-oxo-2-(4,6-dichloro-2-pyrimidyl)pentanenitrile
(214) 4-[5-(2-chloro-4-trifluoromethylphenoxy)-2-chlorophenoxy]-3-oxo-2-(3-methoxymethylphenyl)pentanenitrile
(216) 4-[5-(2,4-dichlorophenoxy)-2-chlorophenoxy]-3-oxo-2-methylpentanenitrile
(218) 4-[5-(2-fluoro-4-chlorophenoxy)-2-chlorophenoxy]-3-oxo-2-cyanopentanenitrile
(220) 4-[5-(6-trifluoromethyl-2-naphtoxy)-2-chlorophenoxy]-3-oxo-2-(2,4-dichlorophenyl)pentanenitrile (222) 4-[5-(7-chloro-2-naphtoxy)-2-chlorophenoxy]-3-oxo-2-(3-chlorophenyl)pentanenitrile
(224) 4-[5-(7-methoxy-2-naphtoxy)-2-chlorophenoxy]-3-oxo-2-(5-methyl-2-thienyl)pentanenitrile
(226) 4-[5-(6-chloro-2-quinoxalinyloxy)-2-chlorophenoxy]-3-oxo-2-(1-tetrahydrofurfuryl)pentanenitrile
(228) 4-[5-(6-chloro-2-quinoxalinyloxy)-2-chlorophenoxy]-3-oxo-2-(3-trifluoromethylphenyl)pentanenitrile
(230) 4-[5-(6-chloro-2-quinoxalinyloxy)-2-chlorophenoxy]-3-oxo-2-(2,4-dichlorophenyl)pentanenitrile
(232) 4-[5-(2-chloro-4-trifluoromethylphenoxy)-2-chlorophenoxy]-3-oxo-2-(2,4-diclorophenyl)butyronitrile
(234) 4-[5-(2-chloro-4-trifluoromethylphenoxy)-2-chlorophenoxy]-3-oxo-2-(2,4-diclorophenyl)-2-methylpentanenitrile
(236) 4-[5-(2-chloro-4-methylphenoxy)-2-chlorophenoxy]-3-oxo-2-benzoylpentanenitrile
(238) 4-[5-(2-chloro-4-nitrophenyl)-2-chlorophenoxy]-3-oxo-2-(3,4-dichlorophenyl)pentanenitrile
(240) 4-[5-(4-trifluoromethylphenylthio)-2-chlorophenoxy]-4-methyl-3-oxo-2-(2-propinyl)pentanenitrile
(242) 4-[5-(4-trifluoromethylphenylthio)-2-chlorophenylthio]-4-methyl-3-oxo-2-cyano-2-methylpentanenitrile
(244) 4-[5-(3-chloro-5-trifluoromethyl-2-pyridyloxy)-2-chlorophenylthio]-3-oxo-2-(2,4-dichlorophenyl)pentanenitrile
(246) 4-[5-(5-trifluoromethyl-2-pyridyloxy)-2-chlorophenoxy]-3-oxo-2-(2-chloro-4-methylphenyl)pentanenitrile
(248) 4-[5-(5-fluoro-2-pyridyloxy)-2-chlorophenylthio]-3-oxo-2-methylthiomethylbutyronitrile
(250) 4-[5-(5-fluoro-3-methyl-2-pyridyloxy)-2-chlorophenylthio]-4-methyl-3-oxo-2-trifluoromethylbutyronitrile
(252) 4-[5-(3-chloro-5-trifluoromethyl-2-pyridyloxy)-2-chlorophenoxy]-4-methyl-3-oxo-2-(2,4-dichlorophenyl)-pentanenitrile
(254) 4-[5-(3-chloro-5-trifluoromethyl-2-pyridyloxy)-2-chlorophenoxy]-4-methyl-3-oxo-2-(2,4-dichlorophenyl)-2-methylpentanenitrile
(256) 4-[5-(2-chloro-4-trifluoromethylphenoxy)-2-chlorophenoxy]-3-oxo-2-(pyrrolidinylcarbonyl)pentanenitrile
(258) 4-[5-(2-chloro-4-trifluoromethylphenoxy)-2-chlorophenoxy]-3-oxo-2-(piperidinocarbonyl)pentanenitrile
(260) 4-[5-(2-chloro-4-trifluoromethylphenoxy)-2-chlorophenoxy]-3-oxo-2-[(1-cycloheptylamino)carbonyl]pentanenitrile
(262) 4-[5-(2-chloro-4-trifluoromethylphenoxy)-2-chlorophenoxy]-3-oxo-2-(morpholinocarbonyl)pentanenitrile
(264) 4-[5-(2-chloro-4-trifluoromethylphenoxy)-2-chlorophenoxy]-3-oxo-2-(4-methylpiperidinocarbonyl)pentanenitrile
(266) 4-[5-(2-chloro-4-trifluoromethylphenoxy)-2-chlorophenoxy]-3-oxo-2-(N-methoxycarbonyl-N-methylaminocarbonyl)pentanenitrile
(268) 4-[5-(2-chloro-4-trifluoromethylphenoxy)-2-chlorophenoxy]-3-oxo-2-(N,N-dimethylaminocarbonyl)pentanenitrile
(270) 4-[5-(2-chloro-4-trifluoromethylphenoxy)-2-chlorophenoxy]-3-oxo-2-(N-methyl-N-phenylaminocarbonyl)pentanenitrile
(272) 4-[5-(2-chloro-4-trifluoromethylphenoxy)-2-chlorophenoxy]-3-oxo-2-(N-ethyl-N-phenylaminocarbonyl)-pentanenitrile
(274) 4-[5-(2-chloro-4-trifluoromethylphenoxy)-2-chlorophenoxy]-3-oxo-2-(N-isopropyl-N-phenylaminocarbonyl)pentanenitrile
(276) 4-[5-(2-chloro-4-trifluoromethylphenoxy)-2-chlorophenoxy]-3-oxo-2-(3,5-dimethylpiperidinocarbonyl)pentanenitrile
(278) 4-[5-(2-chloro-4-trifluoromethylphenoxy)-2-chlorophenoxy]-3-oxo-2-[N-methyl-N-(2,4-dichlorophenyl)aminocarbonyl]pentanenitrile
(280) 4-[5-(6-chloro-2-quinoxalinyloxy)-2-chlorophenoxy]-3-oxo-2-(N-ethoxymethyl-N-methylaminocarbonyl)pentanenitrile
(282) 4-[5-(6-trifluoromethyl-2-naphthoxy)-2-chlorophenoxy]-3-oxo-2-(N-methoxyethyl-N-methylaminocarbonyl)pentanenitrile
(284) 4-[5-(3-chloro-5-trifluoromethyl-2-pyridyloxy)-2-chlorophenoxy]-3-oxo-2-(N-methylaminocarbonyl)pentanenitrile
(286) 4-[5-(6-chloro-2-quinoxalinyloxy)-2-chlorophenoxy]-3-oxo-2-(piperidinocarbonyl)pentanenitrile
(288) 4-[5-(6-chloro-2-quinoxalinyloxy)-2-chlorophenoxy]-3-oxo-2-(N-ethyl-N-methoxyaminocarbonyl)pentanenitrile
(290) 4-[5-(2-benzothiazolyl)-2-chlorophenoxy]-3-oxo-2-(piperidinocarbonyl)pentanenitrile
(292) 4-[5-(2-chloro-4-trifluoromethylphenoxy)-2,4-dichlorophenoxy]-3-oxo-2-(2,4-dichlorophenyl)pentanenitrile
(294) 4-[5-(2-chloro-4-trifluoromethylphenoxy)-2,4-dichlorophenoxy]-3-oxo-2-(5-trifluoromethyl-2-pyridyl)pentanenitrile
(296) 4-[5-(2-chloro-4-trifluoromethylphenoxy)-2,4-dichlorophenoxy]-3-oxo-2-(piperidinocarbonyl)pentanenitrile
(298) 4-[5-(2-chloro-4-trifluoromethylphenoxy)-2-chloro-4-fluorophenoxy]-3-oxo-2-(2,4-dichlorophenyl)pentanenitrile
(300) 4-[5-(2-chloro-4-trifluoromethylphenoxy)-4-chloro-2-fluorophenoxy]-3-oxo-2-(2,4-dichlorophenyl)pentanenitrile
(302) 4-[5-(2-chloro-4-trifluoromethylphenoxy)-4-chloro-2-nitrophenoxy]-3-oxo-2-(2,4-dichlorophenyl)pentanenitrile
(304) 4-[5-(2,4-dichlorophenoxy)-2-chloro-4-fluorophenoxy]-3-oxo-2-(piperidinocarbonyl)pentanenitrile
(306) 4-[5-(2,4-dichlorophenoxy)-2,4-dichlorophenoxy]-3-oxo-2-(piperidinocarbonyl)pentanenitrile
(308) 4-[5-(4-chloro-2-fluorophenoxy)-2,4-dichlorophenoxy]-3-oxo-2-(piperidinocarbonyl)pentanenitrile
(310) 4-[5-(3-chloro-5-trifluoromethyl-2-pyridyloxy]-3-oxo-2-(pyrrolidinylcarbonyl)pentanenitrile
(312) 4-[5-(3-chloro-5-trifluoromethyl-2-pyridyloxy)-2-chloro-4-fluorophenoxy]-3-oxo-2-(2,4-dichlorophenyl)pentanenitrile
(314) 4-[5-(3-chloro-5-trifluoromethyl-2-pyridyloxy)-2,4-dichlorophenoxy]-3-oxo-2-(2,4-(dichlorophenyl)pentanenitrile
(316) 4-[5-(6-trifluoromethyl-2-naphthoxy)-2-chloro-4-fluorophenoxy]-3-oxo-2-(2,4-dichlorophenyl)pentanenitrile
(318) 4-[5-(6-trifluoromethyl-2-naphthoxy)-2-chloro-4-fluorophenoxy]-3-oxo-2-(piperidinocarbonyl)pentanenitrile
(320) 4-[5-(7-chloro-2-naphthoxy)-2-chloro-4-fluorophenoxy] -3-oxo-2-(piperidinocarbonyl)pentanenitrile (322) 4-[5-(7-chloro-2-naphthoxy)-2-chloro-4-fluorophenoxy]-3-oxo-2-(tetrahydrofurfuryl)pentanenitrile (324) 4-[5-(6-chloro-2-quinoxalinyloxy)-2-chloro-4-fluorophenoxy]-3-oxo-2-(piperidinocarbonyl)pentanenitrile (326) 4-[5-(6-chloro-2-quinoxalinyloxy)-4-chloro-2-fluorophenoxy]-3-oxo-2-(piperidinocarbonyl)pentanenitrile (328) 4-[3-(2-chloro-4-trifluoromethylphenoxy)phenoxy]-3-oxo-2-phenylpentane-nitrile (330) 4-[3-(2-chloro-4-trifluoromethylphenoxy)phenoxy]-3-oxo-2-(3,4-dichlorophenyl)pentanenitrile (332) 4-[3-(2-chloro-4-trifluoromethylphenoxy)phenoxy]-3-oxo-2-(3-bromophenyl)pentanenitrile (334) 4-[3-(2-chloro-4-trifluoromethylphenoxy)phenoxy]-3-oxo-2-(3-trifluoromethylphenyl)pentanenitrile (336) 4-[3-(2-chloro-4-trifluoromethylphenoxy)phenoxy]-3-oxo-2-(4-methoxyphenyl)pentanenitrile (338) 4-[3-(2-chloro-4-trifluoromethylphenoxy)phenoxy]-3-oxo-2-(4-hydroxyphenyl)pentanenitrile (340) 4-[3-(2-chloro-4-trifluoromethylphenoxy)phenoxy]-3-oxo-2-(3-chlorophenyl)pentanenitrile The above compounds are particularly industrially easily produced and have excellent herbicidal activity.

The cyanoketone derivative of the formula (1), provided by the present invention, can be structurally identified by measurements of infrared absorption spectrum (IR), mass spectrum (MS) and $^1$H-nuclear magnetic resonance spectrum ($^1$H-NMR) and elemental analysis. Typical patterns thereof are as follows.

(i) In the measurement of the cyanoketone derivative of the formula (1) for infrared absorption spectrum (IR), a characteristic absorption based on the ether bond is observed at 1,070 to 1,232 cm$^{-1}$, and a characteristic absorption based on the cyano group is observed at 2,200 to 2,220 cm$^{-1}$.

(ii) The cyanoketone derivative of the formula (1) is measured for mass spectrum (MS), and its composition formula corresponding to each peak observed (generally, a value of m/e obtained by dividing an ion molecular weight, m, by a number of charge, e) is calculated, whereby the molecular weight of the cyanoketone compound and the bonding mode of each atomic group in the molecule can be determined. That is, when a sample measured has the formula (1), there are generally observed molecular ion peaks (to be abbreviated as "M$^+$" hereinafter) having strength according to an isotopic abundance depending upon the number of halogen atoms contained in the molecule, and the molecular weight of the sample therefore can be determined. Further, the molecular weight generally appears as a mass number of each ion derived from the sample which has been cleaved in positions indicated by dotted lines in the following formula (5)

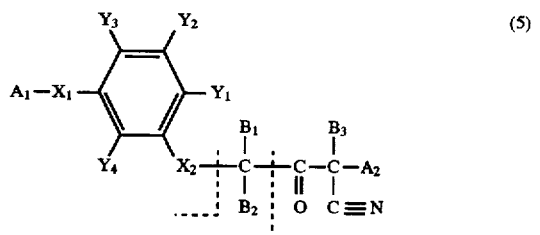

(5)

wherein $A_1$, $X_1$, $X_2$, $Y_1$, $Y_2$, $Y_3$, $Y_4$, $B_1$, $B_2$, $B_3$ and $A_2$ are as defined above.

(iii) The bonding mode of hydrogen bonds in the compound of the present invention, represented by the above formula (1), can be determined by measurement of the compound for $^1$H-nuclear magnetic resonance spectrum ($^1$H-NMR). That is, in the measurement of the compound of the formula (1) in a heavy chloroform solvent, a peak of methine substituted with a cyano group often appears at 5.20 to 5.90 ppm as a multiplet since the carbon atom to which the cyano group is bonded is an asymmetric carbon, and in spite of type of $X_1$, $X_2$, $B_1$, $B_2$, $B_3$ and $A_2$, protons on the phenyl group show a multiplet at 6.00 to 7.50 ppm.

(iv) The weight of each of carbon, hydrogen and nitrogen (and halogen if contained) is determined by elemental analysis, and then by deducting the total sum of recognized weight percentages of these elements from 100, the weight percentage of oxygen can be determined. Accordingly, the composition formula of the compound can be determined.

The cyanoketone derivative of the present invention generally is a light yellow or yellowish brown viscous body or solid at room temperature under atmospheric pressure.

The cyanoketone derivative of the present invention is well-dissolved in organic solvents such as benzene, diethyl ether, ethyl alcohol, N,N-dimethylformamide, dimethylsulfoxide, methylene chloride, chloroform and carbon tetrachloride. However, it is slightly soluble or insoluble in hexane, heptane and water.

The cyanoketone derivative of the formula (1), provided by the present invention, can be produced by any of the following methods (a), (b), (c), (d) and (e).

(a) A method in which a compound of the following formula (6)

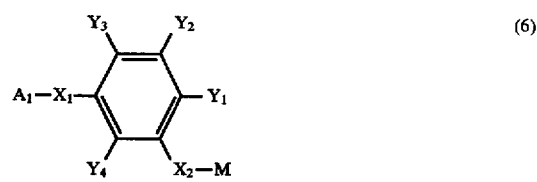

(6)

wherein $A_1$, $X_1$, $X_2$, $Y_2$, $Y_3$ and $Y_4$ are as defined in the formula (1), and M is a hydrogen atom or an alkali metal, and a compound of the following formula (7)

(7)

wherein Z is a halogen atom, and $B_1$, $B_2$, $B_3$ and $A_2$ are as defined in the formula (1), are allowed to react in the presence or absence of a solvent.

(b) A method in which an ester derivative of the following formula (8)

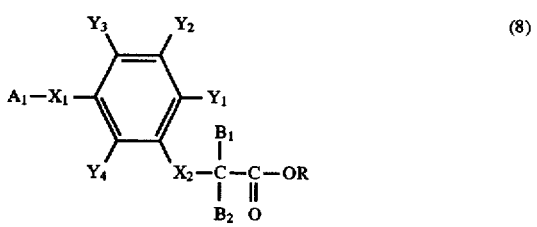

(8)

wherein R is an alkyl group, and $A_1$, $X_1$, $X_2$, $Y_1$, $Y_2$, $Y_3$, $Y_4$, B1 and B2 are as defined in the formula (1).

and a cyano derivative of the following formula (9)

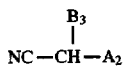
(9)

wherein $B_3$ and $A_2$ are as defined in the formula (1), are allowed to react in the presence or absence of a solvent.

(c) A method in which a compound of the following formula (10)

$A_1-Z$ (10)

wherein Z is a halogen atom and $A_1$ is as defined in the above formula (1), and a compound of the following formula (11)

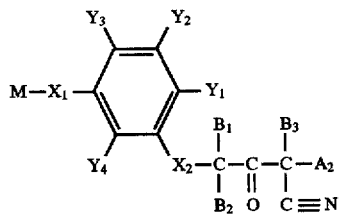
(11)

wherein M is a halogen atom or an alkyl metal, $X_1$, $X_2$, $Y_1$, $Y_2$, $Y_3$, $Y_4$, $B_1$, $B_2$, $B_3$ and $A_2$ are as defined in the formula (1), are allowed to react in the presence or absence of a solvent.

(d) A method in which an acid halide of the following formula (12)

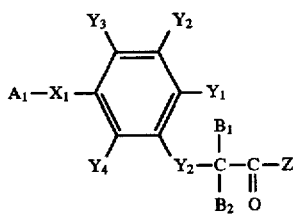
(12)

wherein Z is a halogen atom and $A_1$, $B_1$, $B_2$, $X_1$, $X_2$, $Y_1$, $Y_2$, $Y_3$ and $Y_4$ are as defined in the formula (1), and a compound of the above formula (9) are allowed to react in the presence or absence of a solvent.

(e) When $A_2$ in the formula (1) is a group of

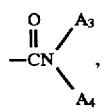

wherein $A_3$ and $A_4$ are as defined in the formula (1), a method in which an acid halide of the following formula (13)

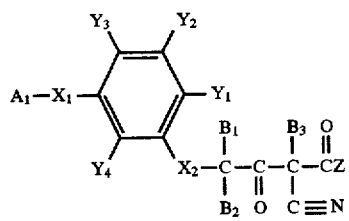
(13)

wherein Z is a halogen atom and $A_1$, $B_1$, $B_2$, $B_3$, $X_1$, $X_2$, $Y_1$, $Y_2$, $Y_3$ and $Y_4$ are as defined in the formula (1), and a compound of the following formula (14)

$A_3-NH-A_4$ (14)

wherein $A_3$ and $A_4$ are as defined in the formula (1), are allowed to react in the presence or absence of a solvent.

In the above method (a), the feed molar ratio of the compounds of the formulae (6) and (7) may be properly determined as required. In general, these compounds are used in an equimolar amount or one of these is used in a little excess, for example, in an amount that is greater than the amount of the other by not more than 20%.

In the above method (b), the feed molar ratio of the ester derivative of the formula (8) and the cyano derivative of the formula (9) may be properly determined as required. In general, these compounds are used in an equimolar amount or one of these is used in a little excess, for example, in an amount that is greater than the amount of the other by not more than 20%.

In the above method (c), the feed molar ratio of the compounds of the formulae (10) and (11) may be properly determined as required. In general, these compounds are used in an equimolar amount or one of these is used in a little excess, for example, in an amount that is greater than the amount of the other by not more than 20%.

In the above method (d), the feed molar ratio of the acid halide of the formula (12) and the compound of the formula (9) may be properly determined as required. In general, these compounds are used in an equimolar amount or one of these is used in a little excess, for example, in an amount that is greater than the amount of the other by not more than 20%.

In the above method (e), the feed molar ratio of the acid halide of the formula (13) and the compound of the formula (14) may be properly determined as required. In general, these compounds are used in an equimolar amount or one of these is used in a little excess, for example, in an amount that is greater than the amount of the other by not more than 20%.

The solvent each in the above methods (a) to (c) is not specially limited, and can be selected from known solvents. Typical examples of the solvent include alcohols such as methanol and ethanol; ethers such as diethyl ether, dimethoxyethane, tetrahydrofuran and dioxane; aromatic solvents such as benzene and toluene, chlorine-containing solvents such as methylene chloride, chloroform and carbon tetrachloride; N,N-dimethylformamide; dimethylsulfoxide; and sulfolane.

The solvent each in the above methods (d) and (e) is not specially limited, and can be selected from known solvents. Typical examples of the solvent include ethers such as diethyl ether, dimethoxyethane, tetrahydrofuran and dioxane; aromatic solvents such as benzene and toluene, chlorine-containing solvents such as methylene chloride, chloroform and carbon tetrachloride; N,N-dimethylformamide; dimethylsulfoxide; and sulfolane.

In the methods (a) and (c), when M is hydrogen, the co-presence of a hydrogen halide binding agent is preferred in order to bind the hydrogen halide produced as a by-product. Also in the methods (d) and (e), the co-presence of a hydrogen halide binding agent is preferred in order to bind the hydrogen halide produced as a by-product. The hydrogen halide binding agent is not specially limited, and can be selected from known agents. Typical examples of the hydrogen halide binding agent preferably usable include trialkylamines such as triethylamine, trimethylamine and tripropylamine; alkyl lithium such as n-butyl lithium, sec.-butyl lithium and tert.-butyl lithium; pyridine, sodium alcoholate, potassium alcoholate, 1,8-diazabicyclo[5,4,0]-7-undecene, sodium carbonate, potassium carbonate, sodium hydroxide, potassium hydroxide, sodium hydrite and potassium hydride.

In the method (b), the condensation agent for removing alcohol from the reaction is not specially limited, and can be selected from known agents. Typical examples of the agent include sodium methylate, potassium methylate, sodium ethylate, potassium ethylate and potassium tert-butylate.

In the methods (a) and (c), examples of the alkali metal, represented by M, in the compounds of the formulae (6) and (11) include sodium, potassium and lithium. Of these metals, sodium and potassium are preferred.

In the methods (a), (c), (d) and (e), examples of the halogen atom, represented by Z, in the compounds of the formulae (7), (10), (12) and (13) include fluorine, chlorine, bromine and iodine.

In the method (b), examples of the alkyl group, represented by R, in the ester derivative of the formula (8) include methyl, ethyl, n-propyl, isopropyl, n-butyl, isobutyl, tert-butyl, pentyl, hexyl, heptyl, octyl, nonyl and decyl. Methyl and ethyl are generally preferably used.

In the methods (a), (b), (c), (d) and (e), the reaction is carried out at a temperature in the range of −78° C. to 200° C., preferably in the range of −50° C. to 150° C., for 0.5 to 45 hours, preferably 0.5 to 24 hours.

The method of isolating the intended product, a cyanoketone derivative, from the reaction system and purifying it is not specially limited, and can be selected from known methods. It is generally preferred to employ a method in which the reaction mixture is added to water, the resultant mixture was subjected to extraction with an organic solvent, and after removing the solvent, the remainder is recrystallized or purified by column chromatography.

A study of the present inventors has showed that the novel cyanoketone derivative of the formula (1), provided by the present invention, has very high herbicidal activity.

According to the present invention, therefore, there is also provided a herbicide containing the cyanoketone derivative of the formula (1) as an effective or active component.

The form for use of the herbicide of the present invention is not specially limited, and can be selected from known forms. For example, it can be used in the form of any one of granules, a dust, an emulsifiable concentrate, a wettable powder, a flowable agent, a tablet, an aerosol and a fuming agent, which are prepared by using an inert solid carrier, a liquid carrier or an emulsification dispersant in combination.

Further, In the preparation of the formulation, there may be incorporated an auxiliary agent such as a wetting agent, a diluent and a surfactant. The herbicide of the present invention can be used in the form of a liquid or a solid to which the above auxiliary agent is properly incorporated. A surfactant is often effective for improvement in the dispersibility of the herbicide in water or an oil.

The above surfactant can be selected from known anionic surfactants, cationic surfactants and nonionic surfactants used for the preparation of general herbicides. Examples of the particularly suitable surfactants include alkylbenzenesulfonic acid, alkylnaphthalenesulfonic acid, fatty acid sulfonate, polyoxyethylene alkylphenyl ether sulfonate, sodium alkylsulfate, sodium lignin sulfonate and polyalkylnaphthalene sulfonate.

Typical examples of the form of the cyanoketone derivative of the formula (1) for use as a herbicide are as follows.

A wettable powder and granules generally contain an inert solid carrier and a surfactant in addition to the active component of the formula (1). The inert solid carrier is generally selected from natural or synthetic inorganic powders. The most preferred are, for example, clays, talc, potassium carbonate, diatomaceous earth and silica. The wettable powder and granules generally contain 1 to 80 parts by weight of the active component, 5 to 98 parts by weight of the inert solid carrier and 1 to 15 parts by weight of the surfactant. Polyvinyl alcohol and sodium carboxymethylcellulose may naturally be incorporated as required.

The emulsifiable concentrate is generally prepared by dissolving the active component and the surfactant in a solvent. The solvent is preferably selected from those which can dissolve the active component. Typical examples of the solvent include xylene, phenoxyethanol, cyclohexane, solvent naphtha, methylnaphthalene and kerosene. The emulsifiable concentrate generally contains 75 to 20 parts by weight of the active component, 10 to 20 parts by weight of the surfactant and 15 to 60 parts by weight of the solvent.

The dust is a product in which the active component is held on a natural or synthetic inorganic powder. The dust is generally prepared by mixing 0.5 to 6 parts by weight of the active component and 99.5 to 94 parts by weight of the inorganic powder.

The flowable agent is a suspension product prepared by suspending the active component insoluble in water, and adding a dispersant to disperse the suspended active component in water. It is the most widely employed embodiment to suspend 20 to 50% by weight of the active component.

The fuming agent is prepared by incorporating a heat generating agent and a heat generation adjuster. The heat generating agent is selected from nitrates, nitrites, guanidine salts and potassium chlorate. The heat generation adjuster is selected from alkali metal salts and potassium nitrates.

The novel cyanoketone derivative of the formula (1) has remarkably high herbicidal activity and is effective against a variety of broad-leaved weeds. Examples of the weeds against which the herbicidal activity is generally effective include upland soil weeds such as common puralane, carpetweed, tufted knotweed, goosefoot, common lamb's quarters, livid amaranth, Japanese mugwort, creeping woodsorred, field bindweed, shepherdspurse, nipplewort, catchweed bedstraw and field sorrel.

The cyanoketone derivative of the formula (1) is a novel compound which has high selectivity, i.e., remarkably high herbicidal activity against broad leaved weeds and safety for graminous plants. Therefore, it has characteristic features in that it is completely harmless to crops such as rice, wheat, barley, corn, etc., even when it is used in a high dosage. When the compound of the formula (1), provided by the invention, is sprayed as a herbicide to gramineous plants, not only the use of it as a soil-applied herbicide is effective, but the use of it as a foliar-applied herbicide is also effective.

in general, the suitable dosage as an active component of the herbicide of the present invention is in the range of 0.05 to 20.0 kg/h, preferably 0.10 to 6.0 kg/h.

The present invention will be explained further in detail hereinafter by reference to Examples. The present invention, however, shall not be limited to these Examples.

EXAMPLE 1

Production of 4-[5-(2-chloro-4-trifluoromethylphenoxy)-2-nitrophenoxy]-3-oxo-2-(2-pyridyl)pentanenitrile (compound No. 100):

2-[5-2-Chloro-4-trifluoromethylphenoxy)-2-nitrophenoxy]propionic acid chloride (2.12 g), 0.65 g of 2-pyridineacetonitrile and 20 ml of anhydrous toluene were charged, and 0.79 g of pyridine was added dropwise to the solution. The mixed solution was stirred at room temperature for 24 hours, and then concentrated with a rotary evaporator. The concentrate was acidified with a 10% hydrochloric acid aqueous solution, and extracted with ethyl acetate, followed by concentrating the extract.

The residue was recrystallized from ether-ethyl acetate to obtain 1.06 g of compound No. 100. The yield was 41.9%. The results of analysis of compound No. 100 are shown in Table 1.

EXAMPLE 2

Production of 4-[5-(2-chloro-4-trifluoromethylphenoxy)-2-nitrophenoxy]-3-oxo-2-(2,4-dichlorophenyl)-pentanenitrile (compound No. 102)

A solution of 0.93 g of 2,4-dichlorophenylacetonitrile in 30 ml of anhydrous tetrahydrofuran (hereinafter abbreviated as "THF") was cooled to −78° C. To this solution was added 3.5 ml of a 1.6M"BuLi-hexane solution. Then, a THF solution of 2.12 g of 2-[5-(2-chloro-4-trifluoromethylphenoxy)-2-nitrophenoxy]propionic acid chloride was added thereto dropwise. The mixed solution was stirred for 30 minutes, then acidified with a 10% hydrochloric acid aqueous solution, and extracted with ethyl acetate. The ethyl acetate layer was dried over anhydrous magnesium sulfate, filtered and concentrated with a rotary evaporator.

The residue was purified by silica gel chromatography to obtain 0.75 g of compound No. 102. The yield was 26.3%. The results of analysis of compound No. 102 are shown in Table 1.

EXAMPLE 3

Production of 4-[5-(2-chloro-4-trifluoromethylphenoxy)-2-nitrophenoxy]-3-oxo-2-(3,4-dichlorophenyl)pentanenitrile (compound No. 104)

Ethyl 2-[5-(2-chloro-4-trifluoromethylphenoxy-2-nitro]propionate (2.16 g) and 0.93 g of 2,3-dichlorophenylacetonitrile were added to a solution of 0.35 g of metallic sodium in 50 ml of ethanol, and the mixture was refluxed under heat for 4 hours. The reaction liquid was concentrated, and a 10% hydrochloric acid aqueous solution was added to the residue. The mixture was extracted with chloroform, and the extract was concentrated. The residue was purified by silica gel chromatography to obtain 1.86 g of compound No. 104 which was a pale yellow viscous substance. The yield was 65.0%. The results of analysis of compound No. 104 are shown in Table 1.

EXAMPLE 4

Production of 4-[5-(3-chloro-5-trifluoromethyl-2-pyridyloxy)-2-nitrophenylthio]-3-oxo-2-(2,4-dichlorophenyl)pentanenitrile (compound No. 148)

2,3-Dichloro-5-trifluoromethylpyridine (1.08 g), 2.05 g of 1-cyano-1-(2,4-dichlorophenyl)-3-(5-hydroxy-2-nitrophenylthio)-2-butanone and 2.07 g of potassium carbonate were refluxed in 50 ml of acetonitrile under heat at 80° C. for 3 hours. The reaction liquid was filtered, and the filtrate was concentrated. A 10% hydrochloric acid aqueous solution was added to the residue, and the mixture was extracted with chloroform, followed by concentrating the extract. The residue was purified by silica gel chromatography to obtain 1.62 g of compound No. 148 which was a pale yellow viscous substance. The yield was 55.0%. The results of analysis of compound No. 148 are shown in Table 1.

EXAMPLE 5

Production of 4-[5-(2-chloro-4-trifluoromethylphenoxy)-2-nitrophenoxy]-3-oxo-2-(4-methylpiperadinylcarbonitrile)pentanenitrile (compound No. 168)

A solution of 2.45 g of 4-[5-(2-chloro-4-trifluoromethylphenoxy)-2-nitrophenoxy]-2-cyano-3-oxopentanoyl chloride in 20 ml of dimethoxyethane was added dropwise to a solution of 0.5 g of N-methylpiperadine, 0.87 g of triethylamine and 30 ml of dimethoxyethane. Then, the mixed solution was stirred at room temperature for 6 hours. The reaction liquid was removed, and the residue was extracted with chloroform, followed by concentrating the extract. The residue was purified by silica gel chromatography to obtain 2.11 g of compound No. 168 which was a pale yellow viscous substance. The yield was 76.2%. The results of analysis of compound No. 168 are shown in Table 1.

EXAMPLE 6

Compounds Nos. 116, 122, 196, 212, 218 and 294 were produced in the same manner as in Example 1.

Compounds Nos. 106, 108, 110, 112, 114, 118, 120, 124, 126, 128, 136, 138, 140, 142, 144, 146, 160, 162, 164, 166, 180, 182, 190, 198, 202, 204, 206, 208, 210, 214, 216, 220, 222, 224, 226, 232, 234, 236, 238, 240, 242, 256, 258, 260, 262, 276, 278 and 286 were produced in the same manner as in Example 2.

Compounds Nos. 172,174, 176,178, 200, 268, 270, 272, 274, 292, 298, 300, 302, 304, 306, 308, 316, 318, 320, 322, 328, 330, 332, 334, 336, 338 and 340 were produced in the same manner as in Example 3.

Compounds Nos. 130, 132, 134, 150, 152, 154, 156, 158, 194, 228, 230, 244, 246, 248, 250, 252, 254, 290, 296, 310, 312, 314, 324 and 326 were produced in the same manner as in Example 4.

Compounds Nos. 170, 184, 186, 188, 192, 264, 266, 280, 282, 284 and 288 were produced in the same manner as in Example 5.

The results of analysis of the obtained compounds are shown in Table 1. In said Table 1, infrared spectra show only characteristic absorptions ascribable to an ether linkage and a cyano group which were obtained from the measurements, and mass spectra show molecular ion peaks ($M^+$) and fragment peaks cleaved in positions shown in the formula (5) which were in common among all the compounds, these peaks being obtained from the measurements.

TABLE 1

| Compound No. | A₁ | B₁ | B₂ | B₃ | X₁ | X₂ | Y₁ | Y₂ | Y₃ | Y₄ | A₂ | MASS | i.r (cm⁻¹) (C—O—C, CN) | ¹H-NMR |
|---|---|---|---|---|---|---|---|---|---|---|---|---|---|---|
| 100 | 2-Cl, 4-CF₃-phenyl | H | CH₃ | H | O | O | NO₂ | H | H | H | 2-pyridyl | 505(M⁺) 360 332 | 1200 2220 | 1.87(d, 3H) 5.32(q, 1H) 6.40(bs, 1H) 6.60–8.55(m, 6H) |
| 102 | 2-Cl, 4-CF₃-phenyl | H | CH₃ | H | O | O | NO₂ | H | H | H | 2,4-diCl-phenyl | 572(M⁺) 360 332 | 1210 2220 | 1.55–1.90(m, 3H) 5.60–5.20(m, 1H) 5.80(d, 1H) 6.40–8.00(m, 9H) |
| 104 | 2-Cl, 4-CF₃-phenyl | H | CH₃ | H | O | O | NO₂ | H | H | H | 2,3-diCl-phenyl | 572(M⁺) 360 332 | 1180 2210 | 1.30–1.80(m, 3H) 5.20–5.55(m, 1H) 5.80(d, 1H) 6.40–8.00(m, 9H) |
| 106 | 2-Cl, 4-CF₃-phenyl | H | CH₃ | H | O | O | NO₂ | H | H | H | 2,6-diCl-phenyl | 572(M⁺) 360 332 | 1180 2220 | 1.50–1.92(m, 3H) 5.20–5.40(m, 1H) 5.82(d, 1H) 6.40–8.00(m, 9H) |
| 108 | 2-Cl, 4-CF₃-phenyl | H | CH₃ | H | O | O | NO₂ | H | H | H | 3-Cl-phenyl | 538(M⁺) 360 332 | 1170 2220 | 0.92–1.85(m, 3H) 5.20(q, 1H) 5.80(m, 1H) 6.20–8.00(m, 10H) |
| 110 | 2-Cl, 4-CF₃-phenyl | H | CH₃ | H | O | O | NO₂ | H | H | H | 3-Br-phenyl | 583(M⁺) 360 332 | 1190 2210 | 1.22–1.88(m, 3H) 4.60–5.60(m, 1H) 5.80(d, 1H) 6.32–8.00(m, 10H) |

TABLE 1-continued

| Compound No. | $A_1$ | $B_1$ | $B_2$ | $B_3$ | $X_1$ | $X_2$ | $Y_1$ | $Y_2$ | $Y_3$ | $Y_4$ | $A_2$ | MASS | i.r (cm$^{-1}$) (C—O—C, CN) | $^1$H-NMR |
|---|---|---|---|---|---|---|---|---|---|---|---|---|---|---|
| 112 | 2-Cl, 4-CF$_3$-phenyl | H | CH$_3$ | H | O | O | NO$_2$ | H | H | H | phenyl | 504(M$^+$) 360 332 | 1180 2210 | 0.90–1.90(m, 3H) 5.24–5.60(m, 1H) 5.80(bs, 1H) 6.20–8.00(m, 11H) |
| 114 | 2-Cl, 4-CF$_3$-phenyl | H | CH$_3$ | H | O | O | NO$_2$ | H | H | H | 3-CH$_3$-phenyl | 518(M$^+$) 360 332 | 1190 2220 | 0.90–1.90(m, 3H) 2.20(s, 3H) 5.25–5.60(m, 1H) 5.78(bs, 1H) 6.60–7.90(m, 10H) |
| 116 | 2-Cl, 4-CF$_3$-phenyl | H | CH$_3$ | H | O | O | NO$_2$ | H | H | H | 4,6-dichloro-2-methylpyrimidinyl | 575(M$^+$) 360 332 | 1190 2220 | 1.50–1.85(m, 3H) 5.60–6.20(m, 1H) 5.75(bs, 1H) 6.40–8.15(m, 7H) |
| 118 | 2-Cl, 4-CF$_3$-phenyl | H | CH$_3$ | H | O | O | NO$_2$ | H | H | H | 3-OCH$_3$-phenyl | 534(M$^+$) 360 332 | 1170 2210 | 1.00–1.80(m, 3H) 3.80(s, 3H) 5.25–5.60(bs, 1H) 6.65–7.80(m, 10H) |
| 120 | 2-Cl, 4-CF$_3$-phenyl | H | CH$_3$ | H | O | O | NO$_2$ | H | H | —CH$_3$ | | 408(M$^+$) 326 298 | 1190 2210 | 1.00–1.80(m, 3H) 5.80(d, 1H) 5.85(bs, 1H) 6.60–8.00(m, 6H) |
| 122 | 2-F, 4-Cl-phenyl | H | CH$_3$ | H | O | O | NO$_2$ | H | H | —CN | | 403(M$^+$) 310 282 | 1170 2220 | 1.60–1.90(m, 3H) 4.58–5.12(m, 1H) 5.41–5.54(m, 1H) 6.98–7.80(m, 6H) |

TABLE 1-continued

| Compound No. | $A_1$ | $B_1$ | $B_2$ | $B_3$ | $X_1$ | $X_2$ | $Y_1$ | $Y_2$ | $Y_3$ | $Y_4$ | $A_2$ | MASS | i.r (cm$^{-1}$) (C—O—C, CN) | $^1$H-NMR |
|---|---|---|---|---|---|---|---|---|---|---|---|---|---|---|
| 124 | 6-CF$_3$-naphthalen-2-yl | CH | CH$_3$ | H | O | O | NO$_2$ | H | H | H | 2,4-dichlorophenyl | 588(M$^+$) 376 348 | 1170 2220 | 1.58–1.92(m, 3H) 5.58–5.20(m, 1H) 5.80(d, 1H) 6.20(bs, 1H) 6.40–8.04(m, 12H) |
| 126 | 6-Cl-naphthalen-2-yl | CH | CH$_3$ | H | O | O | NO$_2$ | H | H | H | 3-chlorophenyl | 520(M$^+$) 342 314 | 1180 2210 | 1.00–1.90(m, 3H) 5.20–5.55(m, 1H) 6.20(bs, 1H) 6.42–8.10(m, 13H) |
| 128 | 6-CH$_3$O-naphthalen-2-yl | CH | CH$_3$ | H | O | O | NO$_2$ | H | H | H | 2,5-dimethylthiophen-3-yl | 502(M$^+$) 338 310 | 1190 2210 | 1.02–1.90(m, 3H) 2.19(s, 3H) 5.75(d, 1H) 6.25(bs, 1H) 6.30–8.00(m, 11H) |
| 130 | 4-Cl-pyrimidin-2-yl | CH | CH$_3$ | H | O | O | NO$_2$ | H | H | H | —CH$_2$-tetrahydrofuran-2-yl | 486(M$^+$) 334 306 | 1180 2220 | 1.25–2.16(m, 7H) 3.30–3.52(m, 2H) 3.90–4.40(m, 3H) 5.46–5.73(m, 1H) 5.80(d, 1H) 9.05(s, 1H) 6.39–8.20(d, 6H) |
| 132 | 4-Cl-pyrimidin-2-yl | CH | CH$_3$ | H | O | O | NO$_2$ | H | H | H | 3-CF$_3$-phenyl | 546(M$^+$) 334 306 | 1200 2210 | 1.00–1.90(m, 3H) 5.65(d, 1H) 6.20(bs, 1H) 6.40–8.20(m, 10H) 9.10(s, 1H) |
| 134 | 4-Cl-pyrimidin-2-yl | CH | CH$_3$ | H | O | O | NO$_2$ | H | H | H | 2,4-dichlorophenyl | 546(M$^+$) 334 306 | 1200 2220 | 1.20–1.92(m, 3H) 5.20–5.55(m, 1H) 6.40(bs, 1H) 6.60–8.10(m, 9H) 9.08(s, 1H) |
| 136 | 2-Cl-4-CF$_3$-phenyl | H | H | H | O | O | NO$_2$ | H | H | H | 2,4-dichlorophenyl | 558(M$^+$) 346 332 | 1200 2220 | 4.80(d, 2H) 5.20–5.60(m, 1H) 6.40–7.98(m, 9H) |

TABLE 1-continued

| Compound No. | A₁ | B₁ | B₂ | B₃ | X₁ | X₂ | Y₁ | Y₂ | Y₃ | Y₄ | A₂ | MASS | i.r (cm⁻¹) (C—O—C, CN) | ¹H-NMR |
|---|---|---|---|---|---|---|---|---|---|---|---|---|---|---|
| 138 | 4-CF₃, 2-Cl phenyl | CH₃ | H | CH₃ | O | O | NO₂ | H | H | H | 2,4-diCl phenyl | 586(M⁺) 360 332 | 1210 2210 | 1.25–2.11(m, 6H) 5.22–5.62(m, 1H) 6.40–8.10(m, 9H) |
| 140 | 4-CH₃, 2-Cl phenyl | CH₃ | H | H | O | O | NO₂ | H | H | H | C(=O)Ph | 531(M⁺) 360 332 | 1190 2220 | 1.00–1.96(m, 3H) 5.30–5.60(m, 1H) 5.83(bs, 1H) 6.00–8.00(m, 11H) |
| 142 | 4-CF₃, 2-NO₂ phenyl | CH₃ | H | H | O | O | NO₂ | H | H | H | 2,4-diCl phenyl | 583(M⁺) 371 343 | 1210 2220 | 1.60–1.90(m, 3H) 5.20–5.62(m, 1H) 6.00(d, 1H) 6.60–8.20(m, 9H) |
| 144 | 4-CF₃ phenyl | CH₃ | CH₃ | H | S | O | NO₂ | H | H | H | —CH₂C≡CH | 462(M⁺) 356 314 | 1220 2220 | 1.19–1.98(m, 6H) 2.35–2.50(m, 1H) 4.20–4.26(m, 2H) 5.80–6.10(bs, 1H) 6.20(8.00(m, 7H) |
| 146 | 4-CF₃ phenyl | CH₃ | H | CH₃ | S | S | NO₂ | H | H | H | —CN | 465(M⁺) 358 330 | 1210 2210 | 1.20–2.12(m, 6H) 6.20(bs, 1H) 6.40–8.20(m, 7H) |
| 148 | 4-CF₃, 2-Cl pyridyl | CH₃ | H | H | O | S | NO₂ | H | H | H | 2,4-diCl phenyl | 589(M⁺) 377 349 | 1170 2210 | 1.32–1.80(m, 3H) 4.60–5.00(m, 1H) 5.30–5.68(m, 1H) 6.94–7.80(m, 7H) 7.81–8.80(m, 2H) |
| 150 | 4-CF₃ pyridyl | CH₃ | H | H | O | O | NO₂ | H | H | H | 3-CH₃, 4-Cl phenyl | 519(M⁺) 327 299 | 1180 2210 | 2.10–2.45(m, 3H) 4.61(s, 2H) 5.76(s, 1H) 6.95–7.50(m, 7H) |

TABLE 1-continued

| Compound No. | A₁ | B₁ | B₂ | B₃ | X₁ | X₂ | Y₁ | Y₂ | Y₃ | Y₄ | A₂ | MASS | i.r (cm⁻¹) (C—O—C, CN) | ¹H-NMR |
|---|---|---|---|---|---|---|---|---|---|---|---|---|---|---|
| 152 | 2-methyl-5-fluoropyridin-yl | H | H | CH₃ | O | S | NO₂ | H | H | H | —CH₂SCH₃ | 421(M⁺) 279 265 | 1190 2220 | 1.32–2.00(m, 3H) 2.52–2.66(m, 3H) 4.31–4.54(m, 3H) 5.45–5.61(m, 1H) 6.97–8.15(m, 6H) |
| 154 | 3-methyl-5-fluoropyridin-yl | CH₃ | H | CH₃ | O | O | NO₂ | H | H | H | —CF₃ | 441(M⁺) 291 263 | 1180 2220 | 1.15–1.68(m, 6H) 2.51(s, 3H) 5.20–5.60(m, 1H) 6.90–8.00(m, 5H) |
| 156 | 3-chloro-5-CF₃-pyridin-yl | CH₃ | H | CH₃ | O | O | NO₂ | H | H | H | 2,4-dichlorophenyl | 587(M⁺) 361 333 | 1210 2220 | 1.16–1.70(m, 6H) 5.22–5.62(m, 1H) 6.60–8.20(m, 8H) |
| 158 | 3-nitro-5-CF₃-pyridin-yl | CH₃ | CH₃ | CH₃ | O | O | NO₂ | H | H | H | 2,5-dichlorophenyl | 596(M⁺) 370 328 | 1220 2220 | 1.42(s, 3H) 1.64(s, 3H) 2.22(s, 3H) 6.00–8.00(m, 8H) |
| 160 | 3-chloro-5-CF₃-phenyl | H | CH₃ | H | O | O | NO₂ | H | H | H | pyrrolidin-1-yl-carbonyl | 525(M⁺) 360 332 | 1200 2210 | 1.74(d, 3H) 1.80–2.40(bs, 4H) 3.45–4.00(bs, 4H) 5.21(q, 1H) 6.40–8.20(m, 7H) |
| 162 | 3-chloro-5-CF₃-phenyl | H | CH₃ | H | O | O | NO₂ | H | H | H | piperidin-1-yl-carbonyl | 539(M⁺) 360 332 | 1200 2220 | 1.40–1.90(m, 9H) 3.40–4.00(bs, 4H) 5.30(q, 1H) 6.40–8.10(m, 7H) |
| 164 | 3-chloro-5-CF₃-phenyl | H | CH₃ | H | O | O | NO₂ | H | H | H | hexamethyleneimin-1-yl-carbonyl | 567(M⁺) 360 332 | 1180 2220 | 1.40–2.10(m, 11H) 3.404.00(bs, 4H) 5.25(q, 1H) 6.40–8.10(m, 7H) |

TABLE 1-continued

| Compound No. | A₁ | B₁ | B₂ | B₃ | X₁ | X₂ | Y₁ | Y₂ | Y₃ | Y₄ | A₂ | MASS | i.r (cm⁻¹) (C—O—C, CN) | ¹H-NMR |
|---|---|---|---|---|---|---|---|---|---|---|---|---|---|---|
| 166 | Cl, CF₃-phenyl | H | CH₃ | H | O | O | NO₂ | H | H | H | morpholino-C(=O)— | 541(M⁺) 360 332 | 1190 2220 | 1.68(d, 3H) 3.70(s, 8H) 5.18(q, 1H) 6.40–8.00(m, 7H) |
| 168 | Cl, CF₃-phenyl | H | CH₃ | H | O | O | NO₂ | H | H | H | 4-methylpiperazino-C(=O)— | 554(M⁺) 360 332 | 1180 2220 | 0.90–1.90(m, 6H) 2.12–3.10(m, 8H) 5.20(q, 1H) 6.42–8.00(m, 7H) |
| 170 | Cl, CF₃-phenyl | H | CH₃ | H | O | O | NO₂ | H | H | H | —C(=O)N(CH₃)CH₂CO₂CH₃ | 476(M⁺) 360 332 | 1190 2210 | 1.32–1.93(m, 3H) 2.50(s, 3H) 4.20(s, 3H) 5.80(bs, 1H) 6.30–8.00(m, 6H) |
| 172 | Cl, CF₃-phenyl | H | CH₃ | H | O | O | NO₂ | H | H | H | —C(=O)N(CH₃)₂ | 499(M⁺) 360 332 | 1210 2210 | 0.95–1.82(m, 3H) 3.10(d, 6H) 5.25–5.62(m, 1H) 6.00(bs, 1H) 6.60–8.30(m, 6H) |
| 174 | Cl, CF₃-phenyl | H | CH₃ | H | O | O | NO₂ | H | H | H | —C(=O)N(CH₃)Ph | 561(M⁺) 360 332 | 1200 2210 | 1.20–1.90(m, 3H) 3.20(s, 3H) 5.15(q, 1H) 6.40–7.80(m, 12H) |
| 176 | Cl, CF₃-phenyl | H | CH₃ | H | O | O | NO₂ | H | H | H | —C(=O)N(C₂H₅)Ph | 575(M⁺) 360 332 | 1180 2200 | 0.90–1.90(m, 6H) 2.50(q, 2H) 5.20–5.55(m, 1H) 5.90(bs, 1H) 6.50–8.10(m, 11H) |

TABLE 1-continued

| Compound No. | $A_1$ | $B_1$ | $B_2$ | $B_3$ | $X_1$ | $X_2$ | $Y_1$ | $Y_2$ | $Y_3$ | $Y_4$ | $A_2$ | MASS | i.r (cm$^{-1}$) (C—O—C, CN) | $^1$H-NMR |
|---|---|---|---|---|---|---|---|---|---|---|---|---|---|---|
| 178 | 2-Cl-4-CF$_3$-phenyl | H | CH$_3$ | H | O | O | NO$_2$ | H | H | H | -C(=O)-N(CH(CH$_3$)$_2$)-phenyl | 589(M$^+$) 360 332 | 1200 2220 | 1.00-2.00(m, 9H) 2.70(q, 1H) 5.85(bs, 1H) 6.50-8.10(m, 11H) |
| 180 | 2-Cl-4-CF$_3$-phenyl | H | CH$_3$ | H | O | O | NO$_2$ | H | H | H | -C(=O)-N-(3,5-dimethylpiperidinyl) | 567(M$^+$) 360 332 | 1180 2210 | 0.85(d, 6H)1.65(d, 3H) 1.60-2.70(m, 3H) 4.20-4.70(m, 2H) 5.20(q, 1H) 6.40-7.80(m, 6H) |
| 182 | 2-Cl-4-CF$_3$-phenyl | H | CH$_3$ | H | O | O | NO$_2$ | H | H | H | -C(=O)-N(CH$_3$)-(2,4-dichlorophenyl) | 631(M$^+$) 360 332 | 1170 2210 | 1.22-1.92(m, 3H) 3.30(s, 3H) 5.20(q, 1H) 6.40-7.80(m, 10H) |
| 184 | 6-Cl-quinoxalin-2-yl | H | CH$_3$ | H | O | O | NO$_2$ | H | H | H | -C(=O)-N(CH$_3$)-CH$_2$OC$_2$H$_5$ | 525(M$^+$) 342 314 | 1210 2200 | 1.00-1.90(m, 6H) 2.10(s, 3H) 2.22-2.74(m, 4H) 5.20(q, 1H) 6.40-7.90(m, 9H) |
| 186 | 6-CF$_3$-naphthalen-2-yl | H | CH$_3$ | H | O | O | NO$_2$ | H | H | H | -C(=O)-N(CH$_3$)-CH$_2$CH$_2$OCH$_3$ | 559(M$^+$) 376 348 | 1200 2210 | 1.20-1.90(m, 3H) 2.12(s, 3H) 3.48-3.90(m, 4H) 5.30(q, 1H) 6.50-8.00(m, 9H) |
| 188 | 3-Cl-5-CF$_3$-pyridin-2-yl | H | CH$_3$ | H | O | O | NO$_2$ | H | H | H | -C(=O)-N(CH$_3$)-H | 486(M$^+$) 361 333 | 1190 2220 | 1.00-1.98(m, 3H) 2.10(s, 3H) 3.70-3.85(m, 1H) 5.10(q, 1H) 6.40-7.90(m, 5H) |

TABLE 1-continued
| Compound No. | $A_1$ | $B_1$ | $B_2$ | $B_3$ | $X_1$ | $X_2$ | $Y_1$ | $Y_2$ | $Y_3$ | $Y_4$ | $A_2$ | MASS | i.r (cm$^{-1}$) (C—O—C, CN) | $^1$H-NMR |
|---|---|---|---|---|---|---|---|---|---|---|---|---|---|---|
| 190 | 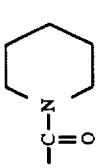 | H | CH$_3$ | H | O | O | NO$_2$ | H | H | H |  | 523(M$^+$) 344 316 | 1170 2200 | 1.42–1.90(m, 13H) 3.40–4.02(m, 1H) 5.40(q, 1H) 6.40–8.10(m, 6H) 9.10(s, 1H) |
| 192 | 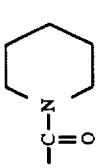 | H | CH$_3$ | H | O | O | NO$_2$ | H | H | H |  | 513(M$^+$) 344 316 | 1180 2210 | 0.90–1.95(m, 6H) 2.50(q, 2H) 3.58(s, 1H)5.12(q, 1H) 6.50–8.00(m, 6H) 9.08(s, 1H) |
| 194 | 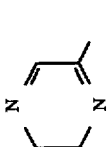 | H | CH$_3$ | H | O | O | NO$_2$ | H | H | H |  | 494(M$^+$) 315 287 | 1190 2200 | 1.44–1.90(m, 13H) 3.40–4.10(m, 1H) 5.40(q, 1H) 6.42–8.00(m, 7H) |
| 196 | 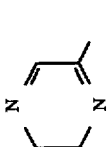 | H | CH$_3$ | H | O | O | Cl | H | H | H | 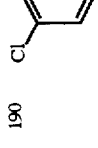 | 494(M$^+$) 349 321 | 1210 2220 | 1.85(d, 3H) 5.22(q, 1H) 6.40(bs, 1H) 6.50–8.55(m, 6H) |
| 198 |  | H | CH$_3$ | H | O | O | Cl | H | H | H | 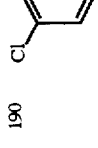 | 561(M$^+$) 349 321 | 1200 2220 | 1.75–1.90(m, 3H) 5.60–5.20(m, 1H) 5.85(d, 1H) 6.42–8.00(m, 9H) |
| 200 |  | H | CH$_3$ | H | O | O | Cl | H | H | H | 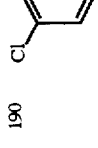 | 561(M$^+$) 349 321 | 1190 2210 | 0.80–1.90(m, 3H) 5.20–5.55(m, 1H) 5.80(d, 1H) 6.40–8.00(m, 9H) |
| 202 |  | H | CH$_3$ | H | O | O | Cl | H | H | H | 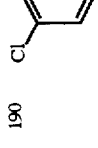 | 561(M$^+$) 349 321 | 1190 2220 | 0.81–1.90(m, 3H) 5.20–5.55(m, 1H) 5.80(d, 1H) 6.40–8.05(m, 9H) |

TABLE 1-continued

| Compound No. | A₁ | B₁ | B₂ | B₃ | X₁ | X₂ | Y₁ | Y₂ | Y₃ | Y₄ | A₂ | MASS | i.r (cm⁻¹) (C—O—C, CN) | ¹H-NMR |
|---|---|---|---|---|---|---|---|---|---|---|---|---|---|---|
| 204 | 2-Cl,4-CF₃-phenyl | H | CH₃ | H | O | O | Cl | H | H | H | 3-Cl-phenyl | 527(M⁺) 349 321 | 1180 2220 | 0.90–1.80(m, 3H) 5.20(q, 1H) 5.80(m, 1H) 6.20–7.90(m, 10H) |
| 206 | 2-Cl,4-CF₃-phenyl | H | CH₃ | H | O | O | Cl | H | H | H | 3-Br-phenyl | 572(M⁺) 349 321 | 1200 2210 | 1.20–1.90(m, 3H) 4.20–5.60(m, 1H) 5.80(d, 1H) 6.30–8.00(m, 10H) |
| 208 | 2-Cl,4-CF₃-phenyl | H | CH₃ | H | O | O | Cl | H | H | H | phenyl | 493(M⁺) 349 321 | 1170 2220 | 1.00–1.90(m, 3H) 5.25–5.60(m, 1H) 5.80(bs, 1H) 6.00–8.00(m, 11H) |
| 210 | 2-Cl,4-CF₃-phenyl | H | CH₃ | H | O | O | Cl | H | H | H | 3-CH₃-phenyl | 507(M⁺) 349 321 | 1180 2220 | 0.90–1.80(m, 3H) 2.21(s, 3H) 5.25–5.60(m, 1H) 5.78(bs, 1H) 6.65–7.80(m, 10H) |
| 212 | 2-Cl,4-CF₃-phenyl | H | CH₃ | H | O | O | Cl | H | H | H | 4,6-dichloro-2-methylpyrimidinyl | 564(M⁺) 349 321 | 1190 2210 | 1.55–1.90(m, 3H) 5.62–6.20(m, 1H) 5.70(bs, 1H) 6.40–8.00(m, 7H) |
| 214 | 2-Cl,4-CF₃-phenyl | H | CH₃ | H | O | O | Cl | H | H | H | 3-OCH₃-phenyl | 523(M⁺) 349 321 | 1180 2210 | 0.90–1.80(m, 3H) 3.70(s, 3H) 5.20–5.60(bs, 1H) 6.65–7.60(m, 10H) |

TABLE 1-continued

| Compound No. | A$_1$ | B$_1$ | B$_2$ | B$_3$ | X$_1$ | X$_2$ | Y$_1$ | Y$_2$ | Y$_3$ | Y$_4$ | A$_2$ | MASS | i.r (cm$^{-1}$) (C—O—C, CN) | $^1$H-NMR |
|---|---|---|---|---|---|---|---|---|---|---|---|---|---|---|
| 216 | 2,4-dichlorophenyl | H | CH$_3$ | H | O | O | Cl | H | H | H | —CH$_3$ | 397(M$^+$) 315 287 | 1190 2200 | 1.00–1.70(m, 3H) 5.75(d, 1H) 5.80(bs, 1H) 6.50–8.00(m, 6H) |
| 218 | 2-F,4-Cl-phenyl | H | CH$_3$ | H | O | O | Cl | H | H | H | —CN | 392(M$^+$) 299 271 | 1170 2210 | 1.20–1.90(m, 3H) 4.40–5.12(m, 1H) 5.40–5.54(m, 1H) 6.88–7.80(m, 6H) |
| 220 | 6-CF$_3$-naphthyl | H | CH$_3$ | H | O | O | Cl | H | H | H | 2,4-dichlorophenyl | 577(M$^+$) 365 337 | 1180 2210 | 1.50–1.92(m, 3H) 5.20–5.60(m, 1H) 5.85(d, 1H) 6.25(bs, 1H) 6.40–8.00(m, 12H) |
| 222 | 6-Cl-naphthyl | H | CH$_3$ | H | O | O | Cl | H | H | H | 3-chlorophenyl | 509(M$^+$) 331 303 | 1170 2210 | 1.10–1.90(m, 3H) 5.30–5.55(m, 1H) 6.10(bs, 1H) 6.32–8.10(m, 13H) |
| 224 | 7-CH$_3$O-naphthyl | H | CH$_3$ | H | O | O | Cl | H | H | H | 2,5-dimethylthienyl | 491(M$^+$) 327 299 | 1200 2210 | 0.98–1.90(m, 3H) 2.10(s, 3H) 5.70(d, 1H) 6.25(bs, 1H) 6.40–8.00(m, 11H) |
| 226 | 5-Cl-pyrazinyl | H | CH$_3$ | H | O | O | Cl | H | H | H | tetrahydrofurfuryl | 475(M$^+$) 323 295 | 1190 2220 | 1.15–1.95(m, 7H) 3.20–3.50(m, 2H) 3.80–4.20(m, 3H) 5.50–5.85(m, 1H) 6.10(d, 1H) 9.05(s, 1H) 6.39–8.20(d, 6H) |
| 228 | 5-Cl-pyrazinyl | H | CH$_3$ | H | O | O | Cl | H | H | H | 3-CF$_3$-phenyl | 535(M$^+$) 323 295 | 1190 2210 | 0.90–1.90(m, 3H) 5.60(d, 1H) 6.25(bs, 1H) 6.50–8.20(m, 10H) 9.10(s, 1H) |

TABLE 1-continued

| Compound No. | A₁ | B₁ | B₂ | B₃ | X₁ | X₂ | Y₁ | Y₂ | Y₃ | Y₄ | A₂ | MASS | i.r (cm⁻¹) (C—O—C, CN) | ¹H-NMR |
|---|---|---|---|---|---|---|---|---|---|---|---|---|---|---|
| 230 | 4-Cl, 1-Cl pyrazine (2-methyl) | H | CH₃ | H | O | O | Cl | H | H | H | 2,4-diCl-phenyl | 535(M⁺) 323 295 | 1190 2220 | 1.15–1.90(m, 3H) 5.15–5.50(m, 1H) 6.35(bs, 1H) 6.70–8.10(m, 9H) 9.08(s, 1H) |
| 232 | 2-Cl, 4-CF₃-phenyl | H | H | H | O | O | Cl | H | H | H | 2,4-diCl-phenyl | 547(M⁺) 335 321 | 1180 2210 | 4.70(d, 2H) 5.10–5.50(m, 1H) 6.40–7.80(m, 9H) |
| 234 | 2-Cl, 4-CF₃-phenyl | CH₃ | H | CH₃ | O | O | Cl | H | H | H | 2,4-diCl-phenyl | 575(M⁺) 349 321 | 1200 2210 | 1.15–2.11(m, 6H) 5.12–5.60(m, 1H) 6.30–8.00(m, 9H) |
| 236 | 2-Cl, 4-CH₃-phenyl | CH | CH₃ | H | O | O | Cl | H | H | H | 2,4-diCl-phenyl | 520(M⁺) 349 321 | 1180 2210 | 0.99–1.90(m, 3H) 5.30–5.55(m, 1H) 5.90(bs, 1H) 6.00–8.00(m, 11H) |
| 238 | 2-NO₂, 4-CF₃-phenyl | CH₃ | CH₃ | H | O | O | Cl | H | H | H | C₆H₅-C(=O)- | 572(M⁺) 360 332 | 1200 2210 | 1.55–1.85(m, 3H) 5.10–5.60(m, 1H) 5.90(d, 1H) 6.30–8.00(m, 9H) |
| 240 | 4-CF₃-phenyl | CH₃ | CH₃ | H | S | O | Cl | H | H | H | —CH₂C≡CH | 451(M⁺) 345 303 | 1200 2220 | 1.09–1.88(m, 6H) 2.20–2.50(m, 1H) 4.10–4.25(m, 2H) 5.80–6.10(bs, 1H) 6.10–7.90(m, 7H) |
| 242 | 4-CF₃-phenyl | CH₃ | H | CH₃ | S | S | Cl | H | H | H | —CN | 454(M⁺) 347 319 | 1190 2210 | 0.90–1.90(m, 6H) 6.10(bs, 1H) 6.40–8.10(m, 7H) |

TABLE 1-continued

| Compound No. | A₁ | B₁ | B₂ | B₃ | X₁ | X₂ | Y₁ | Y₂ | Y₃ | Y₄ | A₂ | MASS | i.r (cm⁻¹) (C—O—C, CN) | ¹H-NMR |
|---|---|---|---|---|---|---|---|---|---|---|---|---|---|---|
| 244 | 3-Cl, 5-CF₃ pyridin-2-yl | CH₃ | H | H | O | S | Cl | H | H | H | 2,4-diCl phenyl | 578(M⁺) 366 338 | 1160 2200 | 1.10–1.80(m, 3H) 4.50–5.00(m, 1H) 5.20–5.40(m, 1H) 6.90–7.80(m, 7H) 7.80–8.80(m, 2H) |
| 246 | 5-CF₃ pyridin-2-yl | CH₃ | H | H | O | O | Cl | H | H | H | 3-Cl, 4-CH₃ phenyl | 518(M⁺) 316 288 | 1170 2210 | 1.90–2.45(m, 3H) 4.60(s, 2H) 5.60(s, 1H) 6.90–7.50(m, 7H) |
| 248 | 5-F pyridin-2-yl | H | H | CH₃ | O | S | Cl | H | H | H | —CH₂SCH₃ | 410(M⁺) 268 254 | 1190 2200 | 1.10–2.00(m, 3H) 2.50–2.70(m, 3H) 4.30–4.42(m, 3H) 5.45–5.65(m, 1H) 7.00–8.15(m, 6H) |
| 250 | 3-CH₃, 5-F pyridin-2-yl | CH₃ | H | H | O | O | Cl | H | H | H | —CF₃ | 430(M⁺) 280 252 | 1180 2210 | 1.00–1.60(m, 6H) 2.55(s, 3H) 5.20–5.60(m, 1H) 6.90–7.90(m, 5H) |
| 252 | 3-Cl, 5-CF₃ pyridin-2-yl | CH₃ | CH₃ | CH₃ | O | O | Cl | H | H | H | 2,4-diCl phenyl | 576(M⁺) 350 322 | 1200 2200 | 1.00–1.70(m, 6H) 5.10–5.65(m, 1H) 6.60–8.10(m, 8H) |
| 254 | 3-NO₂, 5-CF₃ pyridin-2-yl | CH₃ | CH₃ | CH₃ | O | O | Cl | H | H | H | 2,4-diCl phenyl | 585(M⁺) 359 317 | 1190 2200 | 1.35(s, 3H) 1.61(s, 3H) 2.18(s, 3H) 6.00–7.95(m, 8H) |
| 256 | 2-Cl, 4-CF₃ phenyl | H | CH₃ | H | O | O | Cl | H | H | H | pyrrolidin-1-yl-C(=O)— | 514(M⁺) 349 321 | 1190 2200 | 1.70(d, 3H) 1.80–2.30(bs, 4H) 3.40–4.00(bs, 4H) 5.25(q, 1H) 6.40–7.80(m, 7H) |

TABLE 1-continued

| Compound No. | A₁ | B₁ | B₂ | B₃ | X₁ | X₂ | Y₁ | Y₂ | Y₃ | Y₄ | A₂ | MASS | i.r (cm⁻¹) (C—O—C, CN) | ¹H-NMR |
|---|---|---|---|---|---|---|---|---|---|---|---|---|---|---|
| 258 | 2-Cl,4-CF₃-phenyl | H | CH₃ | H | O | O | Cl | H | H | H | —C(=O)—N(piperidine) | 528(M⁺), 349, 321 | 1190, 2210 | 1.20–2.20(m, 9H), 3.40–4.00(bs, 2H), 5.25(q, 1H), 6.40–7.80(m, 6H) |
| 260 | 2-Cl,4-CF₃-phenyl | H | CH₃ | H | O | O | Cl | H | H | H | —C(=O)—N(azepane) | 556(M⁺), 349, 321 | 1180, 2200 | 1.40–2.00(m, 11H), 3.40–4.00(bs, 4H), 5.25(q, 1H), 6.35–7.80(m, 7H) |
| 262 | 2-Cl,4-CF₃-phenyl | H | CH₃ | H | O | O | Cl | H | H | H | —C(=O)—N(morpholine) | 530(M⁺), 349, 321 | 1170, 2210 | 1.69(d, 3H), 3.75(s, 8H), 5.23(q, 1H), 6.40–8.00(m, 7H) |
| 264 | 2-Cl,4-CF₃-phenyl | H | CH₃ | H | O | O | Cl | H | H | H | —C(=O)—N(4-methylpiperazine) | 543(M⁺), 349, 321 | 1170, 2200 | 0.85–1.85(m, 6H), 2.00–2.90(m, 8H), 5.20(q, 1H), 6.30–7.90(m, 7H) |
| 266 | 2-Cl,4-CF₃-phenyl | H | CH₃ | H | O | O | Cl | H | H | H | —C(=O)—N(CH₃)(CO₂CH₃) | 465(M⁺), 349, 321 | 1180, 2200 | 1.25–1.80(m, 3H), 2.40(s, 3H), 4.10(s, 3H), 5.80(bs, 1H), 6.30–7.80(m, 6H) |
| 268 | 2-Cl,4-CF₃-phenyl | H | CH₃ | H | O | O | Cl | H | H | H | —C(=O)—N(CH₃)₂ | 488(M⁺), 349, 321 | 1190, 2210 | 0.90–1.80(m, 3H), 3.12(d, 6H), 5.26–5.65(m, 1H), 6.00(bs, 1H), 6.60–8.20(m, 6H) |

TABLE 1-continued

| Compound No. | A₁ | B₁ | B₂ | B₃ | X₁ | X₂ | Y₁ | Y₂ | Y₃ | Y₄ | A₂ | MASS | i.r (cm⁻¹) (C—O—C, CN) | ¹H-NMR |
|---|---|---|---|---|---|---|---|---|---|---|---|---|---|---|
| 270 | 2-Cl, 4-CF₃ phenyl | H | CH₃ | H | O | O | Cl | H | H | H | N(CH₃)-C(=O)- phenyl | 550(M⁺) 349 321 | 1180 2200 | 1.60(d, 3H) 3.30(s, 3H) 5.10(q, 1H) 6.40–7.80(m, 12H) |
| 272 | 2-Cl, 4-CF₃ phenyl | H | CH₃ | H | O | O | Cl | H | H | H | N(C₂H₅)-C(=O)- phenyl | 564(M⁺) 349 321 | 1190 2190 | 0.90–1.90(m, 6H) 2.52(q, 2H) 5.20–5.50(m, 1H) 5.90(bs, 1H) 6.50–8.00(m, 11H) |
| 274 | 2-Cl, 4-CF₃ phenyl | H | CH₃ | H | O | O | Cl | H | H | H | N(CH(CH₃)₂)-C(=O)- phenyl | 578(M⁺) 349 321 | 1190 2210 | 0.98–1.95(m, 9H) 2.60(q, 1H) 5.80(bs, 1H) 6.50–8.00(m, 11H) |
| 276 | 2-Cl, 4-CF₃ phenyl | H | CH₃ | H | O | O | Cl | H | H | H | 3,5-dimethylpiperidinyl-C(=O)- | 556(M⁺) 349 321 | 1170 2210 | 0.90(d, 6H)1.68(d, 3H) 1.62–2.70(m, 3H) 4.20–4.60(m, 2H) 5.16(q, 1H) 6.40–7.85(m, 6H) |
| 278 | 2-Cl, 4-CF₃ phenyl | H | CH₃ | H | O | O | Cl | H | H | H | N(CH₃)-C(=O)-2,4-dichlorophenyl | 620(M⁺) 349 321 | 1180 2200 | 1.10–1.80(m, 3H) 3.15(s, 3H) 5.15(q, 1H) 6.40–7.85(m, 10H) |

TABLE 1-continued

| Compound No. | $A_1$ | $B_1$ | $B_2$ | $B_3$ | $X_1$ | $X_2$ | $Y_1$ | $Y_2$ | $Y_3$ | $Y_4$ | $A_2$ | MASS | i.r (cm$^{-1}$) (C—O—C, CN) | $^1$H-NMR |
|---|---|---|---|---|---|---|---|---|---|---|---|---|---|---|
| 280 | 4-Cl, pyrimidinyl-phenyl | H | CH$_3$ | H | O | O | Cl | H | H | H | —C(=O)—N(CH$_3$)(CH$_2$OC$_2$H$_5$) | 514(M$^+$) 312 303 | 1200 2210 | 0.95-1.86(m, 6H) 2.12(s, 3H) 2.25-2.84(m, 4H) 5.21(q, 1H) 6.20-7.90(m, 9H) |
| 282 | 6-CF$_3$-naphthyl | H | CH$_3$ | H | O | O | Cl | H | H | H | —C(=O)—N(CH$_3$)(CH$_2$CH$_2$OCH$_3$) | 548(M$^+$) 365 337 | 1190 2210 | 1.10-1.90(m, 3H) 2.16(s, 3H) 3.53-3.98(m, 4H) 5.24(q, 1H) 6.40-8.00(m, 9H) |
| 284 | 3-Cl-6-methyl-pyridinyl(CF$_3$) | H | CH$_3$ | H | O | O | Cl | H | H | H | —C(=O)—N(CH$_3$)(H) | 475(M$^+$) 350 322 | 1200 2220 | 0.98-1.98(m, 3H) 2.08(s, 3H) 3.64-3.85(m, 1H) 5.07(q, 1H) 6.30-7.90(m, 5H) |
| 286 | 4-Cl, pyrimidinyl-phenyl | H | CH$_3$ | H | O | O | Cl | H | H | H | —C(=O)—N(piperidine) | 512(M$^+$) 333 305 | 1180 2200 | 1.32-1.90(m, 13H) 3.30-4.05(m, 1H) 5.35(q, 1H) 6.39-8.10(m, 6H) 9.12(s, 1H) |
| 288 | 4-Cl, pyrimidinyl-phenyl | H | CH$_3$ | H | O | O | Cl | H | H | H | —C(=O)—N(OCH$_3$)(C$_2$H$_5$) | 502(M$^+$) 333 305 | 1180 2200 | 0.90-1.85(m, 6H) 2.45(s, 2H) 3.45(s, 1H) 5.06(q, 1H) 6.40-7.86(m, 6H) 9.05(s, 1H) |
| 290 | benzothiazolyl-methyl | H | CH$_3$ | H | O | O | Cl | H | H | H | —C(=O)—N(piperidine) | 483(M$^+$) 304 276 | 1170 2200 | 1.32-1.85(m, 13H) 3.30-4.10(m, 1H) 5.30(q, 1H) 6.34-7.88(m, 7H) |
| 292 | 2-Cl-4-CF$_3$-phenyl | H | CH$_3$ | H | O | O | Cl | H | H | H | 2,4-dichlorophenyl | 595(M$^+$) 383 355 | 1210 2200 | 1.80-1.95(m, 3H) 5.25-5.62(m, 1H) 5.90(bs, 1H) 6.60-8.20(m, 8H) |

TABLE 1-continued
| Compound No. | $A_1$ | $B_1$ | $B_2$ | $B_3$ | $X_1$ | $X_2$ | $Y_1$ | $Y_2$ | $Y_3$ | $Y_4$ | $A_2$ | MASS | i.r (cm$^{-1}$) (C—O—C, CN) | $^1$H-NMR |
|---|---|---|---|---|---|---|---|---|---|---|---|---|---|---|
| 294 | 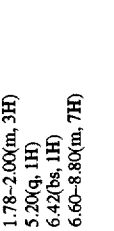 | H | CH$_3$ | H | O | O | Cl | H | Cl | H | 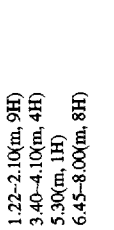 | 597(M$^+$) 383 355 | 1200 2210 | 1.78–2.00(m, 3H) 5.20(q, 1H) 6.42(bs, 1H) 6.60–8.80(m, 7H) |
| 296 | 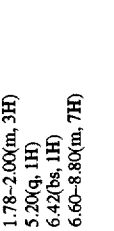 | H | CH$_3$ | H | O | O | Cl | H | Cl | H | 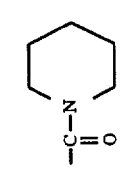 | 562(M$^+$) 383 355 | 1190 2220 | 1.22–2.10(m, 9H) 3.40–4.10(m, 4H) 5.30(m, 1H) 6.45–8.00(m, 8H) |
| 298 | 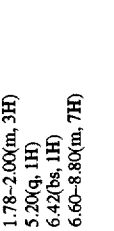 | H | CH$_3$ | H | O | O | Cl | H | F | H | 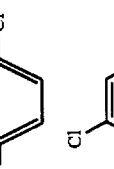 | 579(M$^+$) 367 339 | 1170 2200 | 1.78–1.92(m, 3H) 5.30–5.65(m, 1H) 5.92(bs, 1H) 6.58–8.40(m, 8H) |
| 300 | 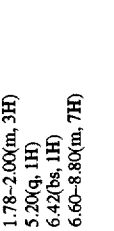 | H | CH$_3$ | H | O | O | F | H | Cl | H | 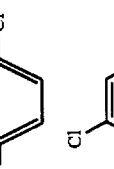 | 579(M$^+$) 367 339 | 1180 2210 | 1.79–1.93(m, 3H) 5.31–5.60(m, 1H) 5.88(bs, 1H) 6.55–8.30(m, 8H) |
| 302 | 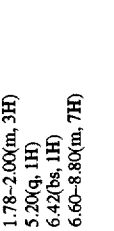 | H | CH$_3$ | H | O | O | NO$_2$ | H | Cl | H | 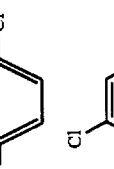 | 606(M$^+$) 394 366 | 1190 2200 | 1.90–2.12(m, 3H) 5.22–5.64(m, 1H) 5.85(bs, 1H) 6.45–8.00(m, 8H) |
| 304 | 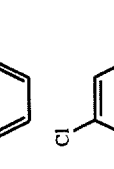 | H | CH$_3$ | H | O | O | Cl | H | F | H | 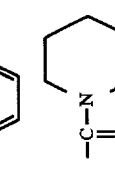 | 512(M$^+$) 333 305 | 1200 2200 | 1.10–2.10(m, 9H) 3.40–4.05(m, 4H) 5.33(m, 1H) 6.50–8.00(m, 6H) |
| 306 | 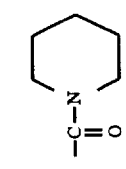 | H | CH$_3$ | H | O | O | Cl | H | Cl | N | 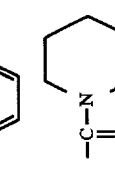 | 512(M$^+$) 333 305 | 1210 2210 | 1.08–2.12(m, 9H) 3.35–4.10(m, 4H) 5.20(m, 1H) 6.50–8.10(m, 6H) |

TABLE 1-continued

| Compound No. | A₁ | B₁ | B₂ | B₃ | X₁ | X₂ | Y₁ | Y₂ | Y₃ | Y₄ | A₂ | MASS | i.r (cm⁻¹) (C—O—C, CN) | ¹H-NMR |
|---|---|---|---|---|---|---|---|---|---|---|---|---|---|---|
| 308 | 2-F-4-Cl-phenyl | H | CH₃ | H | O | O | Cl | H | Cl | N | N-piperidinyl C(=O) | 512(M⁺) 333 305 | 1180 2210 | 1.15–2.20(m, 3H) 3.45–4.20(m, 4H) 5.25(m, 1H) 6.48–8.13(m, 6H) |
| 310 | 3-Cl-5-CF₃-2-pyridyl | H | CH₃ | H | O | O | Cl | H | Cl | N | N-pyrrolidinyl C(=O) | 509(M⁺) 384 356 | 1170 2190 | 1.10–1.80(m, 3H) 1.80–2.30(bs, 4H) 3.42–4.20(bs, 4H) 5.30(q, 1H) 6.60–8.00(m, 5H) |
| 312 | 3-Cl-5-CF₃-2-pyridyl | H | CH₃ | H | O | O | Cl | H | F | N | 2,4-dichlorophenyl | 596(M⁺) 368 340 | 1200 2200 | 1.20–1.90(m, 3H) 4.60–5.10(m, 1H) 5.22–5.42(m, 1H) 7.00–8.80(m, 7H) |
| 314 | 3-Cl-5-CF₃-2-pyridyl | H | CH₃ | H | O | O | Cl | H | F | Cl | 2,4-dichlorophenyl | 596(M⁺) 368 340 | 1210 2200 | 1.18–1.88(m, 3H) 4.65–5.10(m, 1H) 5.30–5.45(m, 1H) 7.05–8.76(m, 7H) |
| 316 | 6-CF₃-2-naphthyl | H | CH₃ | H | O | O | Cl | H | F | H | 2,4-dichlorophenyl | 595(M⁺) 383 355 | 1200 2210 | 1.45–1.90(m, 3H) 5.15–5.60(m, 1H) 5.90(d, 1H) 6.30(bs, 1H) 6.30–8.10(m, 11H) |
| 318 | 6-CF₃-2-naphthyl | H | CH₃ | H | O | O | Cl | H | F | H | N-piperidinyl C(=O) | 562(M⁺) 383 355 | 1190 2210 | 1.20–2.10(m, 13H) 3.30–4.10(m, 1H) 5.45(q, 1H) 6.39–8.10(m, 8H) |
| 320 | 6-Cl-2-naphthyl | H | CH₃ | H | O | O | Cl | H | F | H | N-piperidinyl C(=O) | 527(M⁺) 349 321 | 1200 2210 | 1.25–2.00(m, 13H) 3.35–4.05(m, 1H) 5.38(q, 1H) 6.20–8.10(m, 8H) |

TABLE 1-continued

| Compound No. | A₁ | B₁ | B₂ | B₃ | X₁ | X₂ | Y₁ | Y₂ | Y₃ | Y₄ | A₂ | MASS | i.r (cm⁻¹) (C—O—C, CN) | ¹H-NMR |
|---|---|---|---|---|---|---|---|---|---|---|---|---|---|---|
| 322 | 6-chloronaphth-2-yl | H | CH₃ | H | O | O | F | H | Cl | H | —CH₂-(tetrahydrofuran-2-yl) | 501(M⁺) 349 321 | 1170 2210 | 1.20–2.00(m, 13H) 3.35–4.05(m, 1H) 5.38(q, 1H) 6.20–8.10(m, 8H) |
| 324 | 5-chloropyridin-2-yl | H | CH₃ | H | O | O | Cl | H | F | H | piperidin-1-ylcarbonyl | 520(M⁺) 341 313 | 1190 2200 | 1.28–1.98(m, 13H) 3.27–4.05(m, 1H) 5.37(q, 1H) 6.41–8.10(m, 5H) 9.12(s, 1H) |
| 326 | 5-chloropyridin-2-yl | H | CH₃ | H | O | O | F | H | Cl | H | piperidin-1-ylcarbonyl | 520(M⁺) 341 313 | 1180 2190 | 1.26–1.90(m, 13H) 3.30–4.10(m, 1H) 5.40(q, 1H) 6.28–8.05(m, 6H) 9.10(s, 1H) |
| 328 | 2-chloro-4-trifluoromethylphenyl | H | CH₃ | H | O | O | H | H | H | H | phenyl | 459(M⁺) 315 | 1170 2212 | 1.80–1.20(m, 3H) 4.50–5.10(m, 1H) 5.10–5.71(m, 1H) 6.30–7.90(m, 12H) |
| 330 | 2-chloro-4-trifluoromethylphenyl | H | CH₃ | H | O | O | H | H | H | H | 3,4-dichlorophenyl | 527(M⁺) 315 | 1170 2212 | 1.80–1.21(m, 3H) 5.70–4.60(m, 2H) 6.40–8.00(m, 10H) |
| 332 | 2-chloro-4-trifluoromethylphenyl | H | CH₃ | H | O | O | H | H | H | H | 3-bromophenyl | 539(M⁺) 315 | 1170 2212 | 1.20–1.80(m, 3H) 5.70–4.50(m, 2H) 6.40–8.0(m, 11H) |
| 334 | 2-chloro-4-trifluoromethylphenyl | H | CH₃ | H | O | O | H | H | H | H | 3-trifluoromethylphenyl | 527(M⁺) 315 | 1170 2212 | 1.20–1.80(m, 3H) 4.50–5.20(m, 1H) 5.20–5.70(m, 1H) 6.40–8.20(m, 11H) |

TABLE 1-continued

| Compound No. | A₁ | B₁ | B₂ | B₃ | X₁ | X₂ | Y₁ | Y₂ | Y₃ | Y₄ | A₂ | MASS | i.r (cm⁻¹) (C—O—C, CN) | ¹H-NMR |
|---|---|---|---|---|---|---|---|---|---|---|---|---|---|---|
| 336 | 2-Cl-4-CF₃-phenyl | H | CH₃ | H | O | O | H | H | H | H | 4-OCH₃-phenyl | 489(M⁺) 315 | 1172 2212 | 1.20–1.80(m, 3H) 3.81(s, 3H) 4.60–5.60(m, 2H) 6.30–7.90(m, 11H) |
| 338 | 2-Cl-4-CF₃-phenyl | H | CH₃ | H | O | O | H | H | H | H | 4-OH-phenyl | 475(M⁺) 315 | 1172 2212 | 1.20–1.80(m, 3H) 3.66(s, 1H) 4.50–5.70(m, 2H) 6.30–7.91(m, 11H) |
| 340 | 2-Cl-4-CF₃-phenyl | H | CH₃ | H | O | O | H | H | H | H | 3-Cl-phenyl | 493(M⁺) 315 | 1232 2210 | 1.20–1.80(m, 3H) 4.50–5.70(m, 2H) 6.40–8.00(m, 11H) |

EXAMPLE 7

(Herbicide Preparation Example 1)

Ten (10) parts by weight of the above-mentioned cyanoketone derivative, 2 parts by weight of polyoxyethylene phenyl ether, 40 parts by weight of finely powdered clay and 48 parts by weight of were pulverized and mixed to prepare a 10% wettable powder.

EXAMPLE 8

(Herbicide Preparation Example 2)

Twenty (20) parts by weight of the above-mentioned cyanoketone derivative, 70 parts by weight of xylene and 10 parts by weight of a surfactant were mixed and dissolved to prepare a 20% emulsifiable concentrate.

EXAMPLE 9

(Herbicide Preparation Example 3)

Five (5) parts by weight of the above-mentioned cyanoketone derivative, 90 parts by weight of bentonite (made by Kunimine Kogyo K.K.), and 5 parts by weight of a surfactant were mixed and pulverized to form a paste. The paste was extruded through holes having a diameter of 0.7 mm, dried, and then cut to a length of 1 to 2 mm to prepare 5% granules.

EXAMPLE 10

(Herbicidal effect by foliar application)

Upland farm soil (clay loam) was filled in 1/5,000-are Wagner pots, and seeds of barnyard grass, green foxtail, velvet leaf, livid amaranth and hairy beggarticks were sown 0.5 to 1 cm deep. When these weeds grew to two- or three-leaf stage, 10 ml of a wetting agent was added to each of aqueous solutions prepared by diluting 4 g of each of the wettable powders of the compounds produced according to Example 7 with 1 liter of water, and a predetermined amount of the mixture was sprayed to the foliage such that the active component was rendered in two concentrations shown in Table 2. After the treatment, the weeds were caused to grow in a greenhouse at an average temperature of 25° C. for 2 weeks, and then the herbicidal effects of test compounds were examined.

Other than the compounds of the present invention, the comparative compound of the following formula (15) was also used as a test compound.

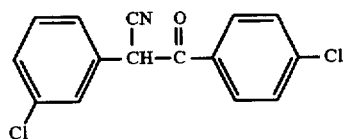

(15)

The results of the examination are shown in Table 2.

The herbicidal effects were evaluated on the basis of the following six rating, 0 to 5.

| | | |
|---|---|---|
| 0 | control of weeds | 0–9% |
| 1 | control of weeds | 10–29% |
| 2 | control of weeds | 30–49% |
| 3 | control of weeds | 50–69% |
| 4 | control of weeds | 70–89% |
| 5 | control of weeds | 90–100% |

TABLE 2-(1)

| Compound No. | Active component g/10a | Barn-yard-grass | Green foxtail | Velvet-leaf | Livid amaranth | Hairy beggerticks |
|---|---|---|---|---|---|---|
| 100 | 500 | 5 | 5 | 5 | 5 | 5 |
|  | 250 | 4 | 5 | 5 | 5 | 5 |
| 102 | 500 | 5 | 5 | 5 | 5 | 5 |
|  | 250 | 4 | 5 | 5 | 5 | 5 |
| 104 | 500 | 5 | 5 | 5 | 5 | 5 |
|  | 250 | 4 | 5 | 5 | 5 | 5 |
| 106 | 500 | 5 | 5 | 5 | 5 | 5 |
|  | 250 | 4 | 4 | 5 | 5 | 5 |
| 108 | 500 | 5 | 5 | 5 | 5 | 5 |
|  | 250 | 4 | 5 | 5 | 5 | 5 |
| 110 | 500 | 5 | 5 | 5 | 5 | 5 |
|  | 250 | 4 | 5 | 5 | 5 | 5 |
| 112 | 500 | 5 | 5 | 5 | 5 | 5 |
|  | 250 | 4 | 5 | 4 | 5 | 5 |
| 114 | 500 | 5 | 5 | 5 | 5 | 5 |
|  | 250 | 4 | 5 | 4 | 5 | 5 |
| 116 | 500 | 5 | 5 | 5 | 5 | 5 |
|  | 250 | 4 | 5 | 4 | 5 | 4 |
| 118 | 500 | 5 | 5 | 5 | 5 | 5 |
|  | 250 | 4 | 5 | 4 | 5 | 4 |
| 120 | 500 | 4 | 5 | 5 | 5 | 5 |
|  | 250 | 4 | 5 | 5 | 5 | 5 |
| 122 | 500 | 5 | 5 | 5 | 5 | 5 |
|  | 250 | 4 | 5 | 5 | 5 | 5 |
| 124 | 500 | 5 | 5 | 5 | 5 | 5 |
|  | 250 | 4 | 4 | 4 | 4 | 4 |
| 126 | 500 | 5 | 5 | 5 | 5 | 5 |
|  | 250 | 4 | 4 | 5 | 5 | 4 |
| 128 | 500 | 5 | 5 | 5 | 5 | 5 |
|  | 250 | 4 | 5 | 5 | 5 | 5 |
| 130 | 500 | 5 | 5 | 5 | 5 | 5 |
|  | 250 | 4 | 4 | 4 | 5 | 4 |
| 132 | 500 | 5 | 5 | 5 | 5 | 5 |
|  | 250 | 4 | 3 | 4 | 5 | 4 |
| 134 | 500 | 5 | 5 | 5 | 5 | 5 |
|  | 250 | 4 | 4 | 5 | 5 | 5 |
| 136 | 500 | 4 | 4 | 4 | 4 | 4 |
|  | 250 | 3 | 3 | 3 | 4 | 3 |
| 138 | 500 | 4 | 4 | 4 | 4 | 4 |
|  | 250 | 3 | 3 | 3 | 4 | 3 |
| 140 | 500 | 5 | 5 | 5 | 5 | 5 |
|  | 250 | 4 | 5 | 5 | 5 | 5 |
| 142 | 500 | 4 | 5 | 5 | 5 | 5 |
|  | 250 | 4 | 4 | 4 | 5 | 5 |
| 144 | 500 | 5 | 5 | 5 | 5 | 5 |
|  | 250 | 4 | 4 | 4 | 5 | 4 |
| 146 | 500 | 5 | 5 | 5 | 5 | 5 |
|  | 250 | 4 | 5 | 5 | 5 | 5 |
| 148 | 500 | 5 | 5 | 5 | 5 | 5 |
|  | 250 | 4 | 4 | 4 | 5 | 4 |
| 150 | 500 | 5 | 5 | 5 | 5 | 5 |
|  | 250 | 4 | 4 | 4 | 5 | 5 |
| 152 | 500 | 5 | 5 | 5 | 5 | 5 |
|  | 250 | 4 | 5 | 5 | 5 | 5 |
| 154 | 500 | 5 | 5 | 5 | 5 | 5 |
|  | 250 | 4 | 4 | 4 | 5 | 4 |
| 156 | 500 | 5 | 5 | 5 | 5 | 5 |
|  | 250 | 4 | 5 | 5 | 5 | 5 |
| 158 | 500 | 5 | 5 | 5 | 5 | 5 |
|  | 250 | 4 | 5 | 5 | 5 | 5 |
| 160 | 500 | 5 | 5 | 5 | 5 | 5 |
|  | 250 | 4 | 5 | 5 | 5 | 5 |
| 162 | 500 | 5 | 5 | 5 | 5 | 5 |
|  | 250 | 4 | 4 | 5 | 5 | 5 |
| 164 | 500 | 5 | 5 | 5 | 5 | 5 |
|  | 250 | 4 | 4 | 5 | 5 | 5 |
| 166 | 500 | 5 | 5 | 5 | 5 | 5 |
|  | 250 | 4 | 4 | 5 | 5 | 5 |
| 168 | 500 | 5 | 5 | 5 | 5 | 5 |
|  | 250 | 4 | 3 | 5 | 5 | 5 |
| 170 | 500 | 5 | 5 | 5 | 5 | 5 |
|  | 250 | 4 | 4 | 4 | 5 | 4 |
| 172 | 500 | 5 | 5 | 5 | 5 | 5 |
|  | 250 | 4 | 4 | 4 | 5 | 4 |
| 174 | 500 | 5 | 5 | 5 | 5 | 5 |

TABLE 2-(1)-continued

| Compound No. | Active component g/10a | Barn-yard-grass | Green foxtail | Velvet-leaf | Livid amaranth | Hairy begger-ticks |
|---|---|---|---|---|---|---|
| 176 | 250 | 4 | 4 | 5 | 5 | 4 |
| | 500 | 5 | 5 | 5 | 5 | 5 |
| 178 | 250 | 3 | 4 | 5 | 5 | 4 |
| | 500 | 5 | 5 | 5 | 5 | 5 |
| 180 | 250 | 3 | 4 | 5 | 5 | 4 |
| | 500 | 5 | 5 | 5 | 5 | 5 |
| 182 | 250 | 4 | 4 | 5 | 5 | 4 |
| | 500 | 5 | 5 | 5 | 5 | 5 |
| 184 | 250 | 4 | 5 | 5 | 5 | 5 |
| | 500 | 5 | 5 | 5 | 5 | 5 |
| 186 | 250 | 4 | 3 | 4 | 5 | 5 |
| | 500 | 5 | 5 | 5 | 5 | 5 |
| 188 | 250 | 4 | 5 | 5 | 5 | 5 |
| | 500 | 5 | 5 | 5 | 5 | 5 |
| 190 | 250 | 3 | 4 | 4 | 5 | 5 |
| | 500 | 5 | 5 | 5 | 5 | 5 |
| 192 | 250 | 4 | 4 | 5 | 5 | 5 |
| | 500 | 5 | 5 | 5 | 5 | 5 |
| 194 | 250 | 4 | 5 | 5 | 5 | 5 |
| | 500 | 5 | 5 | 5 | 5 | 5 |
| 196 | 250 | 4 | 4 | 4 | 5 | 5 |
| | 500 | 5 | 5 | 5 | 5 | 5 |
| 198 | 250 | 4 | 4 | 5 | 5 | 5 |
| | 500 | 5 | 5 | 5 | 5 | 5 |
| 200 | 250 | 4 | 4 | 5 | 5 | 5 |
| | 500 | 5 | 5 | 5 | 5 | 5 |
| 202 | 250 | 4 | 4 | 5 | 5 | 5 |
| | 500 | 5 | 5 | 5 | 5 | 5 |
| 204 | 250 | 3 | 4 | 5 | 5 | 5 |
| | 500 | 5 | 5 | 5 | 5 | 5 |
| 206 | 250 | 4 | 4 | 5 | 5 | 5 |
| | 500 | 5 | 5 | 5 | 5 | 5 |
| 208 | 250 | 3 | 4 | 5 | 5 | 5 |
| | 500 | 5 | 5 | 5 | 5 | 5 |
| 210 | 250 | 3 | 4 | 5 | 5 | 5 |
| | 500 | 5 | 5 | 5 | 5 | 5 |
| 212 | 250 | 4 | 4 | 4 | 5 | 5 |
| | 500 | 5 | 5 | 5 | 5 | 5 |
| 214 | 250 | 4 | 4 | 4 | 5 | 4 |
| | 500 | 5 | 5 | 5 | 5 | 5 |
| 216 | 250 | 4 | 5 | 4 | 5 | 4 |
| | 500 | 5 | 5 | 5 | 5 | 5 |
| 218 | 250 | 3 | 3 | 4 | 5 | 3 |
| | 500 | 5 | 5 | 5 | 5 | 5 |
| 220 | 250 | 4 | 5 | 5 | 5 | 5 |
| | 500 | 5 | 5 | 5 | 5 | 5 |
| 222 | 250 | 3 | 3 | 4 | 5 | 3 |
| | 500 | 5 | 5 | 5 | 5 | 5 |
| 224 | 250 | 4 | 4 | 5 | 5 | 4 |
| | 500 | 5 | 5 | 5 | 5 | 5 |
| 226 | 250 | 4 | 5 | 5 | 5 | 5 |
| | 500 | 5 | 5 | 5 | 5 | 5 |
| 228 | 250 | 4 | 4 | 5 | 5 | 5 |
| | 500 | 5 | 5 | 5 | 5 | 5 |
| 230 | 250 | 4 | 5 | 5 | 5 | 5 |
| | 500 | 5 | 5 | 5 | 5 | 5 |
| 232 | 250 | 4 | 4 | 5 | 5 | 5 |
| | 500 | 5 | 5 | 5 | 5 | 5 |
| 234 | 250 | 4 | 5 | 5 | 5 | 5 |
| | 500 | 5 | 5 | 5 | 5 | 5 |
| 236 | 250 | 3 | 4 | 4 | 5 | 4 |
| | 500 | 5 | 5 | 5 | 5 | 5 |
| 238 | 250 | 4 | 4 | 5 | 5 | 4 |
| | 500 | 5 | 5 | 5 | 5 | 5 |
| 240 | 250 | 4 | 5 | 5 | 5 | 5 |
| | 500 | 5 | 5 | 5 | 5 | 5 |
| 242 | 250 | 4 | 5 | 5 | 5 | 5 |
| | 500 | 5 | 5 | 5 | 5 | 5 |
| 244 | 250 | 4 | 5 | 5 | 5 | 5 |
| | 500 | 5 | 5 | 5 | 5 | 5 |
| 246 | 250 | 4 | 4 | 4 | 5 | 4 |
| | 500 | 5 | 5 | 5 | 5 | 5 |
| 248 | 250 | 4 | 4 | 4 | 5 | 4 |
| | 500 | 5 | 5 | 5 | 5 | 5 |
| 250 | 250 | 4 | 5 | 5 | 5 | 5 |
| | 500 | 5 | 5 | 5 | 5 | 5 |
| 252 | 250 | 3 | 4 | 4 | 5 | 4 |
| | 500 | 5 | 5 | 5 | 5 | 5 |
| 254 | 250 | 4 | 5 | 5 | 5 | 5 |
| | 500 | 5 | 5 | 5 | 5 | 5 |
| 256 | 250 | 4 | 4 | 5 | 5 | 5 |
| | 500 | 5 | 5 | 5 | 5 | 5 |
| 258 | 250 | 4 | 4 | 5 | 5 | 5 |
| | 500 | 5 | 5 | 5 | 5 | 5 |
| 260 | 250 | 4 | 4 | 5 | 5 | 5 |
| | 500 | 5 | 5 | 5 | 5 | 5 |
| 262 | 250 | 4 | 4 | 5 | 5 | 5 |
| | 500 | 5 | 5 | 5 | 5 | 5 |
| 264 | 250 | 4 | 4 | 4 | 5 | 4 |
| | 500 | 5 | 5 | 5 | 5 | 5 |
| 266 | 250 | 3 | 4 | 3 | 5 | 3 |
| | 500 | 5 | 5 | 5 | 5 | 5 |
| 268 | 250 | 4 | 3 | 4 | 5 | 5 |
| | 500 | 5 | 5 | 5 | 5 | 5 |
| 270 | 250 | 4 | 3 | 5 | 5 | 5 |
| | 500 | 5 | 5 | 5 | 5 | 5 |
| 272 | 250 | 4 | 3 | 4 | 5 | 5 |
| | 500 | 5 | 5 | 5 | 5 | 5 |
| 274 | 250 | 4 | 3 | 4 | 5 | 5 |
| | 500 | 5 | 5 | 5 | 5 | 5 |
| 276 | 250 | 4 | 3 | 4 | 5 | 5 |
| | 500 | 5 | 5 | 5 | 5 | 5 |
| 278 | 250 | 3 | 4 | 4 | 5 | 5 |
| | 500 | 5 | 5 | 5 | 5 | 5 |
| 280 | 250 | 4 | 3 | 4 | 5 | 5 |
| | 500 | 5 | 5 | 5 | 5 | 5 |
| 282 | 250 | 4 | 5 | 5 | 5 | 5 |
| | 500 | 5 | 5 | 5 | 5 | 5 |
| 284 | 250 | 3 | 4 | 4 | 5 | 5 |
| | 500 | 5 | 5 | 5 | 5 | 5 |
| 286 | 250 | 3 | 3 | 4 | 5 | 5 |
| | 500 | 5 | 5 | 5 | 5 | 5 |
| 288 | 250 | 4 | 5 | 5 | 5 | 5 |
| | 500 | 5 | 5 | 5 | 5 | 5 |
| 290 | 250 | 3 | 4 | 4 | 5 | 5 |
| | 500 | 5 | 5 | 5 | 5 | 5 |
| 292 | 250 | 3 | 3 | 4 | 5 | 4 |
| | 500 | 5 | 5 | 5 | 5 | 5 |
| 294 | 250 | 4 | 5 | 5 | 5 | 5 |
| | 500 | 5 | 5 | 5 | 5 | 5 |
| 296 | 250 | 3 | 3 | 4 | 5 | 4 |
| | 500 | 5 | 5 | 5 | 5 | 5 |
| 298 | 250 | 3 | 3 | 4 | 5 | 4 |
| | 500 | 5 | 5 | 5 | 5 | 5 |
| 300 | 250 | 3 | 3 | 4 | 5 | 4 |
| | 500 | 5 | 5 | 5 | 5 | 5 |
| 302 | 250 | 4 | 4 | 5 | 5 | 5 |
| | 500 | 5 | 5 | 5 | 5 | 5 |
| 304 | 250 | 4 | 4 | 4 | 5 | 4 |
| | 500 | 5 | 5 | 5 | 5 | 5 |
| 306 | 250 | 4 | 4 | 4 | 5 | 5 |
| | 500 | 5 | 5 | 5 | 5 | 5 |
| 308 | 250 | 4 | 5 | 5 | 5 | 5 |
| | 500 | 5 | 5 | 5 | 5 | 5 |
| 310 | 250 | 3 | 4 | 4 | 5 | 5 |
| | 500 | 5 | 5 | 5 | 5 | 5 |
| 312 | 250 | 3 | 4 | 4 | 5 | 3 |
| | 500 | 5 | 5 | 5 | 5 | 5 |
| 314 | 250 | 4 | 5 | 5 | 5 | 5 |
| | 500 | 5 | 5 | 5 | 5 | 5 |
| 316 | 250 | 4 | 5 | 5 | 5 | 5 |
| | 500 | 5 | 5 | 5 | 5 | 5 |
| 318 | 250 | 3 | 4 | 5 | 5 | 4 |
| | 500 | 5 | 5 | 5 | 5 | 5 |
| 320 | 250 | 4 | 5 | 5 | 5 | 5 |
| | 500 | 5 | 5 | 5 | 5 | 5 |
| 322 | 250 | 4 | 5 | 5 | 5 | 5 |
| | 500 | 5 | 5 | 5 | 5 | 5 |
| 324 | 500 | 5 | 5 | 5 | 5 | 5 |

TABLE 2-(1)-continued

| Compound No. | Active component g/10a | Barnyard-grass | Green foxtail | Velvet-leaf | Livid amaranth | Hairy beggarticks |
|---|---|---|---|---|---|---|
| 326 | 250 | 4 | 5 | 5 | 5 | 5 |
|  | 500 | 5 | 5 | 5 | 5 | 5 |
| 328 | 250 | 3 | 4 | 4 | 5 | 5 |
|  | 500 | 2 | 3 | 3 | 3 | 2 |
| 330 | 250 | 2 | 2 | 2 | 3 | 2 |
|  | 500 | 3 | 3 | 3 | 3 | 3 |
| 332 | 250 | 2 | 2 | 2 | 3 | 3 |
|  | 500 | 3 | 3 | 3 | 3 | 3 |
| 334 | 250 | 2 | 2 | 2 | 3 | 3 |
|  | 500 | 2 | 3 | 3 | 3 | 2 |
| 336 | 250 | 2 | 2 | 2 | 3 | 2 |
|  | 500 | 2 | 3 | 3 | 3 | 3 |
| 338 | 250 | 2 | 2 | 2 | 2 | 2 |
|  | 500 | 2 | 3 | 2 | 3 | 2 |
| 340 | 250 | 2 | 2 | 2 | 2 | 2 |
|  | 500 | 3 | 3 | 2 | 3 | 3 |
|  | 250 | 2 | 2 | 2 | 3 | 3 |
| Comp. Example | 500 | 3 | 3 | 3 | 3 | 2 |
|  | 250 | 2 | 2 | 2 | 2 | 1 |

EXAMPLE 11

(Test for phytotoxicity on crops by foliar application)

Upland farm soil (clay loam) was filled in 1/5,000 are Wagner pots, and seeds of corn, wheat, soybean, beet and sunflower were sown 1.5 to 2 cm deep. When the soybean grew to a primary leaf development stage, 10 ml of a wetting agent was added to each of aqueous solutions prepared by diluting 4 g of each of the wettable powders of the compounds produced according to Example 7 with 1 liter of water, and a predetermined amount of the mixture was sprayed to the foliage such that the active compound was rendered in two concentrations shown in Table 3. After the treatment, the crops were allowed to grow in a greenhouse at an average temperature of 25° C. for 2 weeks, and the phytotoxicity of each of the test compounds on the crops was then examined. The results of the examination are shown In Table 3.

The herbicide injury was evaluated as follows. The ratios of the height and the total weight (air-dried weight) of an applied lot to those of an unapplied lot were calculated. The lowest ratios of these factors were taken as 5, and the phytotoxicity was evaluated on the basis of the following six ratings 0 to 5.

| | |
|---|---|
| 0 | ratio to unapplied lot 100% |
| 1 | ratio to unapplied lot 90–99% |
| 2 | ratio to unapplied lot 80–89% |
| 3 | ratio to unapplied lot 60–79% |
| 4 | ratio to unapplied lot 40–59% |
| 5 | ratio to unapplied lot 0–39% |

TABLE 3-(1)

| Compound No. | Active component g/10a | Corn | Wheat | Soybean | Beet | Sunflower |
|---|---|---|---|---|---|---|
| 100 | 500 | 1 | 1 | 2 | 3 | 2 |
|  | 250 | 0 | 0 | 0 | 0 | 0 |
| 102 | 500 | 1 | 1 | 2 | 3 | 2 |
|  | 250 | 0 | 0 | 0 | 0 | 0 |
| 104 | 500 | 1 | 2 | 1 | 2 | 1 |

TABLE 3-(1)-continued

| Compound No. | Active component g/10a | Corn | Wheat | Soybean | Beet | Sunflower |
|---|---|---|---|---|---|---|
|  | 250 | 0 | 0 | 0 | 0 | 0 |
| 106 | 500 | 0 | 0 | 0 | 1 | 0 |
|  | 250 | 0 | 0 | 0 | 0 | 0 |
| 108 | 500 | 1 | 1 | 2 | 3 | 2 |
|  | 250 | 0 | 0 | 0 | 0 | 0 |
| 110 | 500 | 1 | 1 | 2 | 3 | 2 |
|  | 250 | 0 | 0 | 0 | 0 | 0 |
| 112 | 500 | 0 | 0 | 2 | 2 | 1 |
|  | 250 | 0 | 0 | 0 | 0 | 0 |
| 114 | 500 | 1 | 0 | 2 | 2 | 1 |
|  | 250 | 0 | 0 | 0 | 0 | 0 |
| 116 | 500 | 0 | 1 | 0 | 1 | 1 |
|  | 250 | 0 | 0 | 0 | 0 | 0 |
| 118 | 500 | 0 | 1 | 0 | 1 | 1 |
|  | 250 | 0 | 0 | 0 | 0 | 0 |
| 120 | 500 | 0 | 0 | 0 | 1 | 0 |
|  | 250 | 0 | 0 | 0 | 0 | 0 |
| 122 | 500 | 0 | 0 | 0 | 1 | 1 |
|  | 250 | 0 | 0 | 0 | 0 | 0 |
| 124 | 500 | 0 | 1 | 1 | 2 | 1 |
|  | 250 | 0 | 0 | 0 | 0 | 0 |
| 126 | 500 | 0 | 1 | 1 | 1 | 0 |
|  | 250 | 0 | 0 | 0 | 0 | 0 |
| 128 | 500 | 0 | 1 | 1 | 1 | 0 |
|  | 250 | 0 | 0 | 0 | 0 | 0 |
| 130 | 500 | 0 | 0 | 1 | 1 | 0 |
|  | 250 | 0 | 0 | 0 | 0 | 0 |
| 132 | 500 | 0 | 0 | 1 | 1 | 1 |
|  | 250 | 0 | 0 | 0 | 0 | 0 |
| 134 | 500 | 0 | 1 | 2 | 2 | 2 |
|  | 250 | 0 | 0 | 0 | 0 | 0 |
| 136 | 500 | 0 | 1 | 0 | 1 | 1 |
|  | 250 | 0 | 0 | 0 | 0 | 0 |
| 138 | 500 | 0 | 0 | 1 | 1 | 0 |
|  | 250 | 0 | 0 | 0 | 0 | 0 |
| 140 | 500 | 1 | 1 | 2 | 3 | 2 |
|  | 250 | 0 | 0 | 0 | 0 | 0 |
| 142 | 500 | 1 | 0 | 1 | 1 | 1 |
|  | 250 | 0 | 0 | 0 | 0 | 0 |
| 144 | 500 | 1 | 1 | 2 | 2 | 2 |
|  | 250 | 0 | 0 | 0 | 0 | 0 |
| 146 | 500 | 1 | 1 | 2 | 3 | 2 |
|  | 250 | 0 | 0 | 0 | 0 | 0 |
| 148 | 500 | 1 | 1 | 2 | 3 | 2 |
|  | 250 | 0 | 0 | 0 | 0 | 0 |
| 150 | 500 | 1 | 1 | 2 | 3 | 2 |
|  | 250 | 0 | 0 | 0 | 0 | 0 |
| 152 | 500 | 0 | 0 | 1 | 1 | 1 |
|  | 250 | 0 | 0 | 0 | 0 | 0 |
| 154 | 500 | 0 | 0 | 0 | 1 | 0 |
|  | 250 | 0 | 0 | 0 | 0 | 0 |
| 156 | 500 | 1 | 1 | 2 | 3 | 1 |
|  | 250 | 0 | 0 | 0 | 0 | 0 |
| 158 | 500 | 0 | 1 | 2 | 2 | 2 |
|  | 250 | 0 | 0 | 0 | 0 | 0 |
| 160 | 500 | 1 | 1 | 2 | 3 | 2 |
|  | 250 | 0 | 0 | 0 | 0 | 0 |
| 162 | 500 | 1 | 1 | 2 | 3 | 2 |
|  | 250 | 0 | 0 | 0 | 0 | 0 |
| 164 | 500 | 1 | 2 | 2 | 2 | 2 |
|  | 250 | 0 | 0 | 0 | 0 | 0 |
| 166 | 500 | 1 | 2 | 2 | 2 | 2 |
|  | 250 | 0 | 0 | 0 | 0 | 0 |
| 168 | 500 | 2 | 1 | 1 | 2 | 2 |
|  | 250 | 0 | 0 | 0 | 0 | 0 |
| 170 | 500 | 1 | 1 | 1 | 1 | 0 |
|  | 250 | 0 | 0 | 0 | 0 | 0 |
| 172 | 500 | 1 | 1 | 1 | 1 | 1 |
|  | 250 | 0 | 0 | 0 | 0 | 0 |
| 174 | 500 | 1 | 2 | 2 | 2 | 2 |
|  | 250 | 0 | 0 | 0 | 0 | 0 |
| 176 | 500 | 1 | 1 | 2 | 2 | 0 |
|  | 250 | 0 | 0 | 0 | 0 | 0 |
| 178 | 500 | 1 | 1 | 2 | 2 | 2 |
|  | 250 | 0 | 0 | 0 | 0 | 0 |

TABLE 3-(1)-continued

| Compound No. | Active component g/10a | Corn | Wheat | Soybean | Beet | Sunflower |
|---|---|---|---|---|---|---|
| 180 | 500 | 1 | 1 | 2 | 3 | 2 |
| | 250 | 0 | 0 | 0 | 0 | 0 |
| 182 | 500 | 1 | 1 | 2 | 2 | 1 |
| | 250 | 0 | 0 | 0 | 0 | 0 |
| 184 | 500 | 0 | 0 | 1 | 2 | 1 |
| | 250 | 0 | 0 | 0 | 0 | 0 |
| 186 | 500 | 1 | 0 | 0 | 2 | 1 |
| | 250 | 0 | 0 | 0 | 0 | 0 |
| 188 | 500 | 0 | 0 | 2 | 2 | 2 |
| | 250 | 0 | 0 | 0 | 0 | 0 |
| 190 | 500 | 1 | 1 | 2 | 3 | 2 |
| | 250 | 0 | 0 | 0 | 0 | 0 |
| 192 | 500 | 1 | 1 | 2 | 3 | 2 |
| | 250 | 0 | 0 | 0 | 0 | 0 |
| 194 | 500 | 0 | 0 | 1 | 2 | 1 |
| | 250 | 0 | 0 | 0 | 0 | 0 |
| 196 | 500 | 1 | 1 | 2 | 3 | 2 |
| | 250 | 0 | 0 | 0 | 0 | 0 |
| 198 | 500 | 1 | 1 | 2 | 2 | 2 |
| | 250 | 0 | 0 | 0 | 0 | 0 |
| 200 | 500 | 2 | 2 | 2 | 2 | 2 |
| | 250 | 0 | 0 | 0 | 0 | 0 |
| 202 | 500 | 1 | 1 | 2 | 3 | 2 |
| | 250 | 0 | 0 | 0 | 0 | 0 |
| 204 | 500 | 2 | 1 | 2 | 3 | 2 |
| | 250 | 0 | 0 | 0 | 0 | 0 |
| 206 | 500 | 2 | 1 | 2 | 3 | 2 |
| | 250 | 0 | 0 | 0 | 0 | 0 |
| 208 | 500 | 2 | 1 | 2 | 3 | 2 |
| | 250 | 0 | 0 | 0 | 0 | 0 |
| 210 | 500 | 2 | 1 | 2 | 3 | 2 |
| | 250 | 0 | 0 | 0 | 0 | 0 |
| 212 | 500 | 1 | 1 | 2 | 3 | 2 |
| | 250 | 0 | 0 | 0 | 0 | 0 |
| 214 | 500 | 1 | 1 | 2 | 3 | 2 |
| | 250 | 0 | 0 | 0 | 0 | 0 |
| 216 | 500 | 0 | 0 | 1 | 2 | 1 |
| | 250 | 0 | 0 | 0 | 0 | 0 |
| 218 | 500 | 0 | 0 | 1 | 2 | 2 |
| | 250 | 0 | 0 | 0 | 0 | 0 |
| 220 | 500 | 0 | 0 | 1 | 1 | 1 |
| | 250 | 0 | 0 | 0 | 0 | 0 |
| 222 | 500 | 0 | 0 | 1 | 1 | 1 |
| | 250 | 0 | 0 | 0 | 0 | 0 |
| 224 | 500 | 0 | 0 | 1 | 1 | 2 |
| | 250 | 0 | 0 | 0 | 0 | 0 |
| 226 | 500 | 0 | 0 | 1 | 1 | 1 |
| | 250 | 0 | 0 | 0 | 0 | 0 |
| 228 | 500 | 0 | 1 | 1 | 2 | 1 |
| | 250 | 0 | 0 | 0 | 0 | 0 |
| 230 | 500 | 0 | 0 | 0 | 2 | 1 |
| | 250 | 0 | 0 | 0 | 0 | 0 |
| 232 | 500 | 0 | 1 | 1 | 2 | 1 |
| | 250 | 0 | 0 | 0 | 0 | 0 |
| 234 | 500 | 0 | 0 | 1 | 2 | 1 |
| | 250 | 0 | 0 | 0 | 0 | 0 |
| 236 | 500 | 2 | 1 | 2 | 3 | 2 |
| | 250 | 0 | 0 | 0 | 0 | 0 |
| 238 | 500 | 2 | 1 | 2 | 3 | 2 |
| | 250 | 0 | 0 | 0 | 0 | 0 |
| 240 | 500 | 1 | 1 | 2 | 3 | 2 |
| | 250 | 0 | 0 | 0 | 0 | 0 |
| 242 | 500 | 2 | 2 | 2 | 3 | 2 |
| | 250 | 0 | 0 | 0 | 0 | 0 |
| 244 | 500 | 2 | 1 | 2 | 3 | 2 |
| | 250 | 0 | 0 | 0 | 0 | 0 |
| 246 | 500 | 2 | 1 | 2 | 3 | 2 |
| | 250 | 0 | 0 | 0 | 0 | 0 |
| 248 | 500 | 2 | 1 | 1 | 3 | 2 |
| | 250 | 0 | 0 | 0 | 0 | 0 |
| 250 | 500 | 2 | 1 | 2 | 1 | 2 |
| | 250 | 0 | 0 | 0 | 0 | 0 |
| 252 | 500 | 2 | 1 | 2 | 2 | 2 |
| | 250 | 0 | 0 | 0 | 0 | 0 |
| 254 | 500 | 0 | 1 | 0 | 1 | 2 |
| | 250 | 0 | 0 | 0 | 0 | 0 |
| 256 | 500 | 2 | 1 | 2 | 3 | 2 |
| | 250 | 0 | 0 | 0 | 0 | 0 |
| 258 | 500 | 2 | 1 | 2 | 3 | 2 |
| | 250 | 0 | 0 | 0 | 0 | 0 |
| 260 | 500 | 2 | 1 | 2 | 3 | 1 |
| | 250 | 0 | 0 | 0 | 0 | 0 |
| 262 | 500 | 2 | 1 | 2 | 3 | 1 |
| | 250 | 0 | 0 | 0 | 0 | 0 |
| 264 | 500 | 2 | 1 | 2 | 3 | 2 |
| | 250 | 0 | 0 | 0 | 0 | 0 |
| 266 | 500 | 2 | 1 | 2 | 3 | 2 |
| | 250 | 0 | 0 | 0 | 0 | 0 |
| 268 | 500 | 2 | 1 | 2 | 2 | 1 |
| | 250 | 0 | 0 | 0 | 0 | 0 |
| 270 | 500 | 2 | 1 | 2 | 3 | 2 |
| | 250 | 0 | 0 | 0 | 0 | 0 |
| 272 | 500 | 2 | 1 | 2 | 2 | 2 |
| | 250 | 0 | 0 | 0 | 0 | 0 |
| 274 | 500 | 2 | 1 | 2 | 3 | 2 |
| | 250 | 0 | 0 | 0 | 0 | 0 |
| 276 | 500 | 2 | 1 | 2 | 3 | 2 |
| | 250 | 0 | 0 | 0 | 0 | 0 |
| 278 | 500 | 2 | 1 | 2 | 3 | 2 |
| | 250 | 0 | 0 | 0 | 0 | 0 |
| 280 | 500 | 1 | 1 | 2 | 2 | 1 |
| | 250 | 0 | 0 | 0 | 0 | 0 |
| 282 | 500 | 1 | 1 | 1 | 1 | 1 |
| | 250 | 0 | 0 | 0 | 0 | 0 |
| 284 | 500 | 1 | 1 | 1 | 1 | 1 |
| | 250 | 0 | 0 | 0 | 0 | 0 |
| 286 | 500 | 2 | 1 | 2 | 3 | 2 |
| | 250 | 0 | 0 | 0 | 0 | 0 |
| 288 | 500 | 2 | 1 | 1 | 1 | 1 |
| | 250 | 0 | 0 | 0 | 0 | 0 |
| 290 | 500 | 0 | 0 | 2 | 2 | 1 |
| | 250 | 0 | 0 | 0 | 0 | 0 |
| 292 | 500 | 0 | 0 | 2 | 2 | 1 |
| | 250 | 0 | 0 | 0 | 0 | 0 |
| 294 | 500 | 0 | 0 | 2 | 2 | 1 |
| | 250 | 0 | 0 | 0 | 0 | 0 |
| 296 | 500 | 0 | 0 | 1 | 2 | 1 |
| | 250 | 0 | 0 | 0 | 0 | 0 |
| 298 | 500 | 0 | 0 | 1 | 2 | 0 |
| | 250 | 0 | 0 | 0 | 0 | 0 |
| 300 | 500 | 1 | 0 | 1 | 1 | 1 |
| | 250 | 0 | 0 | 0 | 0 | 0 |
| 302 | 500 | 1 | 1 | 2 | 3 | 2 |
| | 250 | 0 | 0 | 0 | 0 | 0 |
| 304 | 500 | 1 | 0 | 1 | 2 | 0 |
| | 250 | 0 | 0 | 0 | 0 | 0 |
| 306 | 500 | 1 | 0 | 1 | 1 | 1 |
| | 250 | 0 | 0 | 0 | 0 | 0 |
| 308 | 500 | 0 | 0 | 1 | 2 | 0 |
| | 250 | 0 | 0 | 0 | 0 | 0 |
| 310 | 500 | 0 | 0 | 1 | 2 | 1 |
| | 250 | 0 | 0 | 0 | 0 | 0 |
| 312 | 500 | 0 | 0 | 1 | 1 | 1 |
| | 250 | 0 | 0 | 0 | 0 | 0 |
| 314 | 500 | 0 | 0 | 1 | 1 | 1 |
| | 250 | 0 | 0 | 0 | 0 | 0 |
| 316 | 500 | 5 | 5 | 5 | 5 | 5 |
| | 250 | 0 | 0 | 0 | 0 | 0 |
| 318 | 500 | 1 | 1 | 2 | 3 | 1 |
| | 250 | 0 | 0 | 0 | 0 | 0 |
| 320 | 500 | 1 | 1 | 2 | 3 | 1 |
| | 250 | 0 | 0 | 0 | 0 | 0 |
| 322 | 500 | 1 | 1 | 2 | 3 | 1 |
| | 250 | 0 | 0 | 0 | 0 | 0 |
| 324 | 500 | 1 | 2 | 1 | 2 | 1 |
| | 250 | 0 | 0 | 0 | 0 | 0 |
| 326 | 500 | 1 | 1 | 2 | 3 | 1 |
| | 250 | 0 | 0 | 0 | 0 | 0 |
| 328 | 500 | 0 | 0 | 0 | 1 | 0 |
| | 250 | 0 | 0 | 0 | 0 | 0 |

TABLE 3-(1)-continued

| Compound No. | Active component g/10a | Corn | Wheat | Soybean | Beet | Sunflower |
|---|---|---|---|---|---|---|
| 330 | 500 | 0 | 1 | 1 | 1 | 0 |
|  | 250 | 0 | 0 | 0 | 0 | 0 |
| 332 | 500 | 0 | 1 | 0 | 1 | 1 |
|  | 250 | 0 | 0 | 0 | 0 | 0 |
| 334 | 500 | 0 | 0 | 0 | 1 | 0 |
|  | 250 | 0 | 0 | 0 | 0 | 0 |
| 336 | 500 | 0 | 0 | 0 | 1 | 0 |
|  | 250 | 0 | 0 | 0 | 0 | 0 |
| 338 | 500 | 0 | 0 | 0 | 0 | 0 |
|  | 250 | 0 | 0 | 0 | 0 | 0 |
| 340 | 500 | 0 | 1 | 0 | 1 | 1 |
|  | 250 | 0 | 0 | 0 | 0 | 0 |

EXAMPLE 12

(Herbicidal effect by upland soil application)

Upland farm soil (clay loam) was filled in 1/5,000-are Wagner pots, and seeds of barnyard grass, green foxtail, velvet leaf, livid amaranth and hairy beggarticks were sown 0.5 to 1 cm deep. Then, a predetermined amount of each of aqueous solutions prepared by diluting 4 g of each of the wettable powders of the compounds produced according to Example 7 with 1 liter of water was sprayed to the foliage such that the active component was rendered in a concentration shown in Table 4. After the treatment, the weeds were caused to grow in a greenhouse at an average temperature of 25° C. for 4 weeks, and then the herbicidal effects of test compounds were examined.

The results of the examination are shown in Table 4.

The herbicidal effects were evaluated on the same basis as above.

TABLE 4

| Compound No. | Active component g/10a | Barnyard-grass | Green foxtail | Velvet-leaf | Livid amaranth | Hairy beggerticks |
|---|---|---|---|---|---|---|
| 100 | 1000 | 5 | 5 | 5 | 5 | 5 |
| 102 | 1000 | 5 | 5 | 5 | 5 | 5 |
| 104 | 1000 | 5 | 5 | 5 | 5 | 5 |
| 106 | 1000 | 4 | 5 | 5 | 5 | 5 |
| 108 | 1000 | 5 | 5 | 5 | 5 | 5 |
| 110 | 1000 | 5 | 5 | 5 | 5 | 5 |
| 112 | 1000 | 4 | 5 | 5 | 5 | 4 |
| 114 | 1000 | 5 | 5 | 5 | 5 | 5 |
| 116 | 1000 | 4 | 5 | 4 | 5 | 5 |
| 118 | 1000 | 4 | 5 | 4 | 5 | 5 |
| 120 | 1000 | 4 | 4 | 4 | 5 | 4 |
| 122 | 1000 | 4 | 4 | 4 | 5 | 4 |
| 124 | 1000 | 4 | 4 | 5 | 5 | 4 |
| 126 | 1000 | 4 | 4 | 5 | 5 | 4 |
| 128 | 1000 | 4 | 4 | 4 | 4 | 4 |
| 130 | 1000 | 4 | 5 | 4 | 5 | 5 |
| 132 | 1000 | 4 | 5 | 4 | 5 | 5 |
| 134 | 1000 | 4 | 5 | 5 | 5 | 4 |
| 136 | 1000 | 4 | 4 | 4 | 4 | 4 |
| 138 | 1000 | 4 | 4 | 4 | 5 | 4 |
| 140 | 1000 | 5 | 5 | 5 | 5 | 5 |
| 142 | 1000 | 4 | 5 | 4 | 5 | 5 |
| 144 | 1000 | 4 | 5 | 5 | 5 | 5 |
| 146 | 1000 | 4 | 4 | 4 | 4 | 4 |
| 148 | 1000 | 5 | 5 | 5 | 5 | 5 |
| 150 | 1000 | 5 | 5 | 5 | 5 | 5 |
| 152 | 1000 | 4 | 4 | 4 | 4 | 4 |
| 154 | 1000 | 4 | 4 | 5 | 5 | 5 |
| 156 | 1000 | 5 | 5 | 5 | 5 | 5 |
| 158 | 1000 | 4 | 4 | 4 | 4 | 4 |
| 160 | 1000 | 5 | 5 | 5 | 5 | 5 |
| 162 | 1000 | 5 | 5 | 5 | 5 | 5 |
| 164 | 1000 | 5 | 5 | 5 | 5 | 5 |
| 166 | 1000 | 5 | 5 | 5 | 5 | 5 |
| 168 | 1000 | 5 | 5 | 5 | 5 | 5 |
| 170 | 1000 | 5 | 5 | 4 | 5 | 5 |
| 172 | 1000 | 5 | 5 | 4 | 5 | 5 |
| 174 | 1000 | 4 | 5 | 5 | 5 | 5 |
| 176 | 1000 | 4 | 5 | 5 | 5 | 5 |
| 178 | 1000 | 4 | 5 | 5 | 5 | 5 |
| 180 | 1000 | 5 | 5 | 5 | 5 | 5 |
| 182 | 1000 | 4 | 4 | 4 | 4 | 4 |
| 184 | 1000 | 4 | 4 | 5 | 5 | 5 |
| 186 | 1000 | 4 | 4 | 5 | 5 | 5 |
| 188 | 1000 | 5 | 5 | 5 | 5 | 5 |
| 190 | 1000 | 5 | 5 | 5 | 5 | 5 |
| 192 | 1000 | 4 | 4 | 4 | 4 | 4 |
| 194 | 1000 | 4 | 4 | 4 | 5 | 5 |
| 196 | 1000 | 5 | 5 | 5 | 5 | 5 |
| 198 | 1000 | 5 | 5 | 5 | 5 | 5 |
| 200 | 1000 | 5 | 5 | 5 | 5 | 5 |
| 202 | 1000 | 5 | 5 | 5 | 5 | 5 |
| 204 | 1000 | 5 | 5 | 5 | 5 | 5 |
| 206 | 1000 | 5 | 5 | 5 | 5 | 5 |
| 208 | 1000 | 5 | 5 | 5 | 5 | 5 |
| 210 | 1000 | 5 | 5 | 5 | 5 | 5 |
| 212 | 1000 | 4 | 5 | 4 | 5 | 5 |
| 214 | 1000 | 4 | 5 | 4 | 5 | 5 |
| 216 | 1000 | 4 | 4 | 4 | 5 | 4 |
| 218 | 1000 | 4 | 4 | 4 | 4 | 4 |
| 220 | 1000 | 4 | 4 | 5 | 5 | 4 |
| 222 | 1000 | 4 | 4 | 5 | 5 | 4 |
| 224 | 1000 | 4 | 4 | 4 | 4 | 4 |
| 226 | 1000 | 4 | 5 | 4 | 5 | 5 |
| 228 | 1000 | 4 | 4 | 4 | 4 | 4 |
| 230 | 1000 | 4 | 5 | 5 | 5 | 4 |
| 232 | 1000 | 4 | 5 | 4 | 4 | 4 |
| 234 | 1000 | 4 | 4 | 4 | 5 | 4 |
| 236 | 1000 | 5 | 5 | 5 | 5 | 5 |
| 238 | 1000 | 4 | 4 | 4 | 4 | 4 |
| 240 | 1000 | 4 | 4 | 4 | 4 | 4 |
| 242 | 1000 | 4 | 4 | 4 | 4 | 4 |
| 244 | 1000 | 5 | 5 | 5 | 5 | 5 |
| 246 | 1000 | 5 | 5 | 5 | 5 | 5 |
| 248 | 1000 | 4 | 4 | 4 | 4 | 4 |
| 250 | 1000 | 4 | 4 | 4 | 4 | 4 |
| 252 | 1000 | 5 | 5 | 5 | 5 | 5 |
| 254 | 1000 | 4 | 4 | 4 | 4 | 4 |
| 256 | 1000 | 5 | 5 | 5 | 5 | 5 |
| 258 | 1000 | 5 | 5 | 5 | 5 | 5 |
| 260 | 1000 | 5 | 5 | 5 | 5 | 5 |
| 262 | 1000 | 5 | 5 | 5 | 5 | 5 |
| 264 | 1000 | 5 | 5 | 5 | 5 | 5 |
| 266 | 1000 | 5 | 5 | 4 | 5 | 5 |
| 268 | 1000 | 5 | 5 | 4 | 5 | 5 |
| 270 | 1000 | 5 | 5 | 5 | 5 | 5 |
| 272 | 1000 | 4 | 5 | 5 | 5 | 5 |
| 274 | 1000 | 4 | 4 | 4 | 4 | 4 |
| 276 | 1000 | 5 | 5 | 5 | 5 | 5 |
| 278 | 1000 | 4 | 4 | 4 | 4 | 4 |
| 280 | 1000 | 4 | 4 | 5 | 5 | 5 |
| 282 | 1000 | 4 | 4 | 4 | 4 | 4 |
| 284 | 1000 | 4 | 4 | 5 | 5 | 5 |
| 286 | 1000 | 5 | 5 | 5 | 5 | 5 |
| 288 | 1000 | 4 | 4 | 4 | 4 | 4 |
| 290 | 1000 | 4 | 4 | 5 | 5 | 5 |
| 292 | 1000 | 4 | 4 | 4 | 5 | 4 |
| 294 | 1000 | 4 | 4 | 4 | 4 | 4 |
| 296 | 1000 | 4 | 4 | 4 | 4 | 4 |
| 298 | 1000 | 4 | 5 | 5 | 5 | 5 |
| 300 | 1000 | 4 | 5 | 5 | 5 | 5 |
| 302 | 1000 | 5 | 5 | 5 | 5 | 5 |
| 304 | 1000 | 4 | 5 | 5 | 5 | 5 |
| 306 | 1000 | 4 | 5 | 5 | 5 | 5 |

TABLE 4-continued

| Compound No. | Active component g/10a | Barnyard-grass | Green foxtail | Velvet-leaf | Livid amaranth | Hairy beggerticks |
|---|---|---|---|---|---|---|
| 308 | 1000 | 4 | 4 | 4 | 4 | 4 |
| 310 | 1000 | 4 | 4 | 4 | 5 | 5 |
| 312 | 1000 | 4 | 5 | 5 | 5 | 5 |
| 314 | 1000 | 4 | 5 | 5 | 5 | 5 |
| 316 | 1000 | 4 | 4 | 4 | 4 | 4 |
| 318 | 1000 | 4 | 5 | 5 | 5 | 5 |
| 320 | 1000 | 4 | 5 | 4 | 4 | 4 |
| 322 | 1000 | 4 | 4 | 5 | 4 | 4 |
| 324 | 1000 | 4 | 4 | 4 | 5 | 4 |
| 326 | 1000 | 4 | 5 | 5 | 5 | 5 |
| 328 | 1000 | 2 | 2 | 3 | 3 | 2 |
| 330 | 1000 | 3 | 2 | 2 | 3 | 3 |
| 332 | 1000 | 3 | 2 | 2 | 3 | 3 |
| 334 | 1000 | 2 | 2 | 2 | 3 | 2 |
| 336 | 1000 | 2 | 2 | 2 | 2 | 2 |
| 338 | 1000 | 2 | 2 | 2 | 2 | 2 |
| 340 | 1000 | 2 | 3 | 3 | 3 | 3 |

What is claimed is:

1. A cyanoketone derivative of the following formula (1)

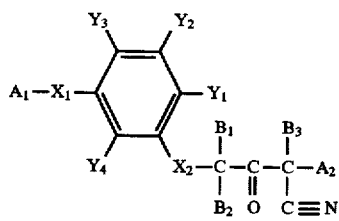

wherein $A_1$ is a substituted or unsubstituted phenyl or naphthyl group, or a substituted or unsubstituted heterocyclic group selected from the group consisting of a 5-membered ring, a 6-membered ring, a 5- and 6-membered fused ring group and a 6- and 6-membered fused ring group, wherein said heterocyclic group contains 1, 2 or 3 hetero atoms which may be the same or different and are selected from the group consisting of oxygen atoms, nitrogen atoms, and sulfur atoms, substituents of said substituted phenyl, naphthyl and heterocyclic groups being selected from the group consisting of a halogen atom, an alkyl group having 1 to 4 carbon atoms a halogenoalkyl group having 1 to 4 atoms, an alkoxy group having 1 to 4 carbon atoms, an alkylthio group having 1 to 4 carbon atoms, an alkoxycarbonyl group having 1 to 6 carbon atoms in the alkyl moiety, a nitro group and a cyano group;

each of $X_1$ and $X_2$ is independently an oxygen or sulfur atom;

each of $B_1$, $B_2$ and $B_3$ is independently a hydrogen atom or alkyl group having 1 to 6 carbon atoms;

$Y_1$ is a hydrogen atom, a nitro group or a halogen atom, each of $Y_2$, $Y_3$ and $Y_4$ is independently a hydrogen atom, a halogen atom or an alkyl group having 1 to 6 carbon atoms;

$A_2$ is a substituted or unsubstituted alkyl group having 1 to 6 carbon atoms, an alkenyl group having 2 to 6 carbon atoms, an alkynyl group having 2 to 6 carbon atoms, an alkoxy group having 1 to 4 carbon atoms, an alkylthio group having 1 to 4 carbon atoms, an alkoxycarbonyl group having 1 to 6 carbon atoms in the alkyl moiety, a cyano group, a substituted or unsubstituted benzoyl group, a group as defined in $A_1$ or a group

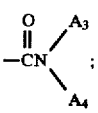

substituents of said substituted alkyl group and said substituted benzoyl group are selected from the group consisting of a halogen atom, an alkoxy group having 1 to 4 carbon atoms, an alkylthio group having 1 to 4 carbon atoms, a cyano group, and a tetrahydrofuryl group;

each of $A_3$ and $A_4$ is, independently, selected from the group consisting of a hydrogen atom, a substituted or unsubstituted alkyl group having 1 to 6 carbon atoms, an alkenyl group having 2 to 6 carbon atoms, an alkynyl group having 2 to 6 carbon atoms, an alkoxy group having 1 to 4 carbon atoms, an alkylthio group having 1 to 4 carbon atoms, an alkoxycarbonyl group having 1 to 6 carbon atoms in the alkyl moiety and a group as defined in $A_1$; or both $A_3$ and $A_4$ together with the nitrogen atom to which they are bonded form a saturated or unsaturated ring of from 2 to 8 carbon atoms which may contain at least one additional nitrogen or oxygen atom and, when one of $B_1$ and $B_2$ is a hydrogen atom and the other is alkyl, the compound of the formula (1) is an R- or S-enantiomers with regard to the asymmetric carbon to which $B_1$ and $B_2$ are bonded or a mixture of these enantiomers.

2. A cyanoketone derivative of claim 1 wherein $A_1$ is a substituted or unsubstituted phenyl group.

3. A cyanoketone derivative of claim 1 wherein each of $X_1$ and $X_2$ are oxygen atoms.

4. A cyanoketone derivative of claim 1 wherein $Y_1$ is a halogen atom or a nitro group.

5. A cyanoketone derivative of claim 1 wherein each of $Y_2$, $Y_3$ and $Y_4$ are hydrogen atoms.

6. A cyanoketone derivative of claim 1 wherein one of $B_1$ and $B_2$ is a hydrogen atom and the other is an alkyl group.

7. A cyanoketone derivative of claim 1 wherein $B_3$ is a hydrogen atom.

8. A cyanoketone derivative of claim 1 wherein $A_2$ is a substituted or unsubstituted phenyl group or additional nitrogen or oxygen group of

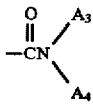

in which $A_3$ and $A_4$ together form a saturated or unsaturated ring which may contain additional nitrogen or oxygen hetero atom.

9. A herbicidal composition comprising a herbicidally effective amount of a cyanoketone derivative of claim 1 and an inert carrier.

10. A herbicide composition of claim 9 wherein $Y_1$ of the formula (1) is a halogen atom or a nitro group.

11. A herbicide composition of claim 9 wherein each of $Y_2$, $Y_3$ and $Y_4$ of the formula (1) are hydrogen atoms.

12. A herbicide composition of claim 9 wherein one of $B_1$ and $B_2$ is a hydrogen atom and the other is an alkyl group.

13. A herbicide composition of claim 9 wherein $B_3$ is a hydrogen atom.

14. A herbicide composition of claim 9 wherein $A_2$ of the formula (1) is a substituted or unsubstituted phenyl group or a group of

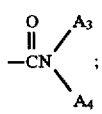

in which $A_3$ and $A_4$ together form a saturated or unsaturated ring which may contain a hereto atom.

15. A method of inhibiting the growth of broad-leaved weeds comprising applying a herbicidally effective amount of the herbicide of claim 9 to the locus of weed growth.

16. The method of claim 15 wherein said herbicide is applied to the soil.

17. The method of claim 15 wherein said herbicide is applied to the foliage of said weeds.

18. The method of claim 15 wherein the herbicide of claim 9 is applied to a locus where broad-leaved weeds grow or are anticipated to grow.

19. A cyanoketone derivative of claim 1 wherein $A_1$ is said substituted or unsubstituted heterocyclic group which is selected from the group consisting of furyl, thienyl, pyrrolyl, imidazolyl, pyrazolyl, oxazolyl, thiazolyl, isooxazolyl, isothiazolyl, pyridyl, pyranyl, thiopyranyl, piperazinyl, pyrimidinyl, triazinyl, benzofuranyl, benzothienyl, indolyl, benzimidazolyl, benzothiazolyl, benzoxazolyl, oxazolopyridinyl, thiazolopyridinyl, quinolyl, quinoxalinyl and quinazolinyl.

20. A cyanoketone derivative of claim 8 wherein $A_3$ and $A_4$ together with the nitrogen atom to which they are bonded form a ring selected from the group consisting of ethyleneimino, pyrrolidyl, pyrrolyl, pyrrolinyl, pyrazyl, pyrazolinyl, imidazolyl, triazolyl, piperidino, morpholino, piperazinyl, and indolyl.

21. A cyanoketone derivative of claim 2 wherein $A_2$ is said substituted or unsubstituted phenyl group.

22. A cyanoketone derivative of claim 2 wherein each of $X_1$ and $X_2$ are oxygen atoms; $Y_1$ is a halogen atom or a nitro group; each of $Y_2$, $Y_3$ and $Y_4$ are hydrogen atoms; one of $B_1$ and $B_2$ is an alkyl group and the other is a hydrogen atom; $B_3$ is a hydrogen atom; and $A_2$ is said substituted or unsubstituted phenyl group or the group

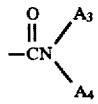

in which $A_3$ and $A_4$ together with the nitrogen atom to which they are bonded form said saturated or unsaturated ring and which may contain said additional hetero atom.

23. A herbicide composition of claim 9 in the form of a wettable powder or granules comprising from 1 to 80 parts by weight of the cyanoketone derivative of formula (1), 5 to 98 parts by weight of an inert solid carrier and 1 to 15 parts by weight of a surfactant.

24. A herbicide composition of claim 9 in the form of an emulsifiable concentrate comprising from 75 to 20 parts by weight of the cyanoketone derivative of formula (1), 10 to 20 parts by weight of a surfactant and 15 to 60 parts by weight of a solvent in which the cyanoketone derivative is soluble.

25. A herbicide composition of claim 9 in the form of a flowable agent comprising a suspension of from 20 to 50% by weight of the cyanoketone derivative of formula (1) in water and a dispersant in an amount effective to disperse the suspended cyanoketone derivative in water.

26. The method of claim 15 which comprises applying from about 0.05 to 20.0 kilograms per hectare of the cyanoketone derivative to the locus of weed growth.

27. A cyanoketone derivative of claim 1 which is

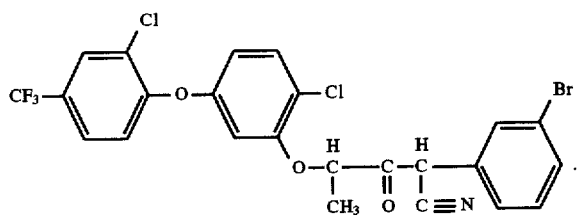

28. A cyanoketone derivative of formula (1) according to claim 1 which is selected from the group consisting of

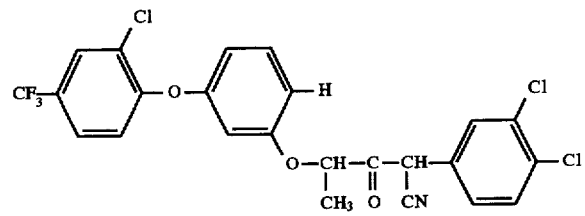

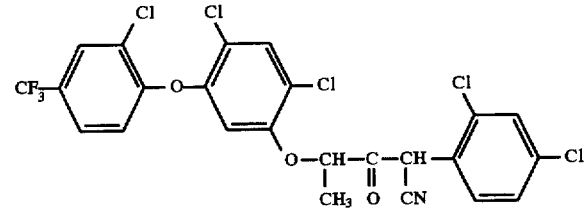

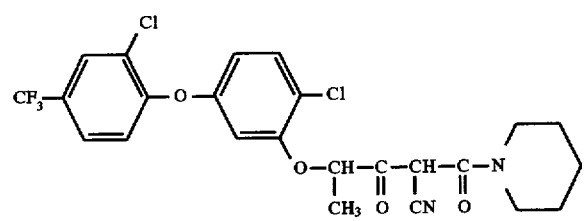

* * * * *